United States Patent
Anderson, Jr. et al.

(10) Patent No.: US 9,650,323 B2
(45) Date of Patent: May 16, 2017

(54) TRI-SUBSTITUTED AROMATIC-CONTAINING ADDITIVES AND SURFACTANTS AND METHODS FOR USE

(71) Applicant: RHODIA OPERATIONS, Paris (FR)

(72) Inventors: Eugene J. Anderson, Jr., Marlton, NJ (US); Derek Pakenham, Hamilton, NJ (US); Nemesio Martinez-Castro, Bristol, PA (US); Jose P. Ruiz, Burlington, NJ (US); Michael Rhodes, Chalfont, PA (US); Lichang Zhou, Lawrenceville, NJ (US)

(73) Assignee: RHODIA OPERATIONS, Paris (FR)

( * ) Notice: Subject to any disclaimer, the term of this patent is extended or adjusted under 35 U.S.C. 154(b) by 0 days.

(21) Appl. No.: 14/661,814

(22) Filed: Mar. 18, 2015

(65) Prior Publication Data

US 2015/0267035 A1    Sep. 24, 2015

Related U.S. Application Data

(60) Provisional application No. 61/954,857, filed on Mar. 18, 2014, provisional application No. 61/954,852, filed on Mar. 18, 2014.

(51) Int. Cl.

| | | |
|---|---|---|
| *C07C 41/03* | (2006.01) | |
| *C07C 43/205* | (2006.01) | |
| *C08F 22/12* | (2006.01) | |
| *C08K 3/04* | (2006.01) | |
| *C08K 5/13* | (2006.01) | |
| *C07C 69/54* | (2006.01) | |
| *C07C 37/14* | (2006.01) | |
| *C08F 20/30* | (2006.01) | |
| *C08F 220/30* | (2006.01) | |

(52) U.S. Cl.
CPC .......... *C07C 43/2055* (2013.01); *C07C 37/14* (2013.01); *C07C 41/03* (2013.01); *C07C 69/54* (2013.01); *C08F 20/30* (2013.01); *C08F 22/12* (2013.01); *C08K 3/04* (2013.01); *C08K 5/13* (2013.01); *C08F 2220/306* (2013.01)

(58) Field of Classification Search
CPC .......... C07C 37/14; C07C 41/03; C07C 69/54; C08F 22/12; C08F 20/30
USPC .......................................... 524/375; 568/640
See application file for complete search history.

(56) References Cited

U.S. PATENT DOCUMENTS

| | | |
|---|---|---|
| 3,937,283 A | 2/1976 | Blauer et al. |
| 4,579,670 A | 4/1986 | Payne |
| 5,551,516 A | 9/1996 | Norman et al. |
| 5,770,760 A | 6/1998 | Robinson |

FOREIGN PATENT DOCUMENTS

| | | | |
|---|---|---|---|
| EP | 0186255 A2 | | 2/1985 |
| EP | 0177111 A2 | | 4/1985 |
| EP | 0149173 A1 | | 7/1985 |
| JP | 60229969 A2 | | 11/1985 |
| JP | 61241370 A2 | | 10/1986 |
| JP | 11-263929 | * | 9/1999 |
| JP | 2004505127 A | | 2/2004 |
| RU | 2246504 C1 | | 2/2005 |
| WO | 0035863 A1 | | 6/2000 |
| WO | 2013072696 A1 | | 5/2013 |

OTHER PUBLICATIONS

Machine translation of JP 11-263929 (1999).*
G. Poehlen, "Emulsion Polymerization", Encyclopedia of Polymer Science and Engineering, vol. 6, pp. 1-51 (John Wiley & Sons, Inc., NY, NY, 1986).
A. S. Sarac, "Redox Polymerization", Progress in Polymer Science 24 (1999), pp. 1149-1204.
Edited by Raymond E. Kirk and Donald F. Othmer, Encyclopedia of Chemical Technology, Third Edition, John Wiley & Sons, vol. 16, pp. 248-273 (entitled "Nuts"), Copyright 1981.
"Oilfield Applications", Encyclopedia of Polymer Science and Engineering, vol. 10, pp. 328-366 (John Wiley & Sons, Inc., New York, NY., 1987).

* cited by examiner

*Primary Examiner* — Edward Cain

(57) ABSTRACT

Disclosed are novel tri-substituted aromatic-alkoxylated surface active compounds. Also provided is a method of preparing an aqueous coating composition such as a latex paint including the above components.

21 Claims, No Drawings

TRI-SUBSTITUTED AROMATIC-CONTAINING ADDITIVES AND SURFACTANTS AND METHODS FOR USE

CROSS-REFERENCE TO RELATED APPLICATIONS

This application claims the benefit of U.S. Provisional Patent Application No. 61/954,857 filed Mar. 18, 2014, incorporated herein by reference in its entirety, and claims the benefit of U.S. Provisional Patent Application No. 61/954,852 filed Mar. 18, 2014, incorporated herein by reference in its entirety.

FIELD OF THE INVENTION

The present invention relates to novel tri-substituted aromatic surfactants, additives, emulsifiers, and the like, methods of preparing, as well as compositions and methods using such compositions in various applications.

BACKGROUND OF THE INVENTION

Dispersant additives assist to disperse small or fine particles into a liquid medium. Such disperants are useful in coatings, plastics, cosmetics, and the like. Suitable dispersants are able to disperse, as finely and efficiently as possible, such fine or small particles into a liquid medium, which remains stable over a certain time. One problem with currently available dispersants, however, is that the dispersion of fine particles in liquids is unstable in that the particles tend to agglomerate or flocculate causing changes in properties, e.g., varing shades of color, unequal pigmentation, changes in rheology, as well as other undesireable properties, over time in the product where disperability is desired.

In particular, coatings can have a wide variety of miscellaneous additives, which are usually added in small amounts, yet provide a significant effect on the product. Some examples include additives to modify surface tension, improve flow properties, improve the finished appearance, increase wet edge, improve pigment stability, impart antifreeze properties, control foaming, control skinning, etc. Other types of additives include catalysts, thickeners, stabilizers, emulsifiers, texturizers, adhesion promoters, UV stabilizers, flatteners (de-glossing agents), biocides to fight bacterial growth, and the like. Additives normally do not significantly alter the percentages of individual components in a formulation In the paints and coatings additives market, surfactants are used as wetting, anti-foaming and dispersing agents.

SUMMARY OF THE INVENTION

Additives or thickeners may be used in a variety of liquid systems including aqueous systems such as paints, aqueous inks, and personal care products and compositions for treating subterranean formations. The additives improve the rheological properties by also affecting the dispersion, suspension and emulsification of pigments, binders and other solids within a vehicle.

The present invention relates to the use of a particular family of alkoxylated compounds with bulky hydrophobic groups, e.g., alkoxylated tri-substituted phenols, for improving properties in a composition such as, in paints and coatings, dispersability, freeze-thaw stability, open time, low temperature film formation, stain resistance, film gloss, hiding and scrub resistance, foam resistance, block resistance, adhesion and water sensitivity, among others.

In one aspect, described herein are additives, emulsifiers, dispersants and/or surfactants according to structure (D.I):

(D.I).

$R^{12}$ is absent or is a bivalent linking group,
$R^{13}$ is bivalent polyether group,
$R^{14}$ is absent or is a bivalent linking group;
$R^{18}$ is an anionic, nonionic or cationic end group; and
$R^{11}$ is according to structure D.XII

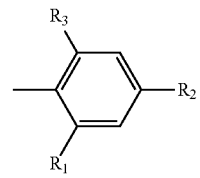

D.XII wherein $R_1$, $R_2$ and $R_3$ are independently selected from H, any of following structures D.XIIa, D.XIIb, D.XIIc, D.XIId:

D.XIIIa

D.XIIIb

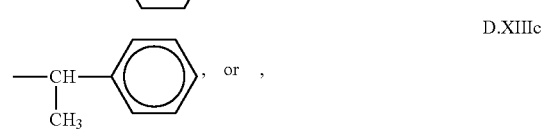
D.XIIIc

D.XIIId or a $C_2$-$C_{30}$ branched or linear alkyl group or alkenyl group;
wherein at least one of $R_1$, $R_2$ and $R_3$ is the $C_2$-$C_{30}$ branched or linear alkyl group or alkenyl group, and at least one of $R_1$, $R_2$ and $R_3$ is selected from structure D.XIIa, D.XIIb, D.XIIc, or D.XIId.

In one embodiment, $R^{18}$ is —OH, —OCH$_3$, —OC$_2$H$_5$, —OC$_3$H$_7$, —OC$_4$H$_9$, —OC$_5$H$_{11}$, —OC$_6$H$_{13}$, —Cl, —Br, —CN, Phosphonate (—PC$_3^-$M$^+$), Phosphate (PO$_4^-$M$^+$), Sulfate (SO$_4^-$M$^+$), Sulfonate (SC$_3^-$M$^+$), carboxylate (COO$^-$M$^+$), a nonionic group, or a quaternary ammonium ion, wherein M+ is a cation including but not limited to H$^+$, Na$^+$, NH$_4^+$, K$^+$ or Li$^+$. In one embodiment, $R^{18}$ is alkyl, hydroxyalkyl, alkoxyalkyl, cycloalkyl, aryl, arylalkyl, or aryloxy. In another embodiment, $R^{18}$ is (C$_1$-C$_{22}$)alkyl, (C$_1$-C$_{22}$)hydroxyalkyl, (C$_2$-C$_{22}$)alkoxyalkyl, (C$_6$-C$_{24}$)cycloalkyl, (C$_6$-C$_{40}$)aryl, or (C$_7$-C$_{40}$)arylalkyl, more typically (C$_2$-C$_{12}$)alkyl In one embodiment, $R^{18}$ is an inorganic or organic substituent group, such as, for example, alkyl, alkenyl, aryl, aralkyl, alkaryl, a hetero atom, or heterocyclyl, or with one or more functional groups such as hydroxyl, carbonyl, carboxyl, amino, imino, amido, phosphonic acid, sulphonic acid, or inorganic and organic esters thereof, such as, for example, sulphate or phosphate, or salts thereof.

In another aspect, described herein are compounds according to structure (D.I):

$R^{12}$ is absent or is a bivalent linking group,
$R^{13}$ is bivalent polyether group,
$R^{14}$ is absent or is a bivalent linking group;
$R^{18}$ is an anionic, nonionic or cationic end group; and
$R^{11}$ a tri-substituted aromatic group according to the structure D.XII

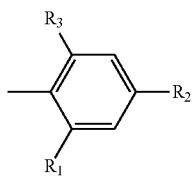

D.XII wherein $R_1$, $R_2$ and $R_3$ are independently selected from the following structures D.XIIa, D.XIIb, D.XIIc, D.XIId:

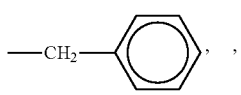

D.XIIIa

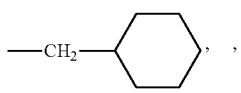

D.XIIIb

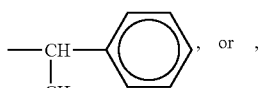

D.XIIIc

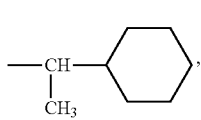

D.XIIId or a $C_2$-$C_{30}$ branched or linear alkyl group or alkenyl group;
wherein at least one of $R_1$, $R_2$ and $R_3$ is the $C_2$-$C_{30}$ branched or linear alkyl group or alkenyl group, and at least one of $R_1$, $R_2$ and $R_3$ is selected from structure D.XIIa, D.XIIb, D.XIIc, or D.XIId.

In one embodiment, $R_{12}$ is —$(CH_2)_xO$—, wherein x is an integer from 1 to 20 (e.g., use of styrenated benzyl alcohols)

In another embodiment, $R_{12}$ is —$CH_2CH(OH)CH_2O$— or —$CH_2CH(CH_2OH)O$— (e.g., use of epichlorohydrin as coupling agent)

In one embodiment, $R_{13}$ is:
—[CH($R_{20}$)CH($R_{21}$)O]$_x$— wherein x is an integer of from 0 to 100, and $R_{20}$ and $R_{21}$ are independently selected from any of the following:
H; —$CH_2OH$; phenyl; —$CH_2Cl$;
a $C_1$-$C_{30}$ straight or branched alkyl or alkenyl;
—$CH_2OR_{22}$ wherein $R_{22}$ is $C_1$-$C_{30}$ straight or branched alkyl or alkenyl, phenyl, or alkyl substituted phenyl; or
R'COOCH$_2$— where R' is $C_1$-$C_{30}$ straight or branched alkyl or alkenyl.

In one embodiment, $R^{18}$ is —OH, —$OCH_3$, —$OC_2H_5$, —$OC_3H_7$, —$OC_4H_9$, —$OC_5H_{11}$, —$OC_6H_{13}$, —Cl, —Br, —ON, Phosphonate (—$PC_3^-M^+$), Phosphate ($PO_4^-M^+$), Sulfate ($SO_4^-M^+$), Sulfonate ($SC_3^-M^+$), carboxylate ($COO^-$ $M^+$), a nonionic group, or a quaternary ammonium ion, wherein M+ is a cation including but not limited to $H^+$, $Na^+$, $NH_4^+$, $K^+$ or $Li^+$.

In one embodiment, $R^{18}$ is an inorganic or organic substituent group, such as, for example, alkyl, alkenyl, aryl, aralkyl, alkaryl, a hetero atom, or heterocyclyl, or with one or more functional groups such as hydroxyl, carbonyl, carboxyl, amino, imino, amido, phosphonic acid, sulphonic acid, or inorganic and organic esters thereof, such as, for example, sulphate or phosphate, or salts thereof.

The invention is also directed to a homogeneous, pourable liquid which improves properties in aqueous coatings, for example, improved water sensitivity. These improved properties are due to a reduction in the use level of the thickeners as described herein, needed to achieve a desired rheological profile.

The aqueous coating compositions of the invention typically include at least one latex polymer derived from at least one monomer, for example acrylic monomers. The at least one latex polymer in the aqueous coating composition can be a pure acrylic, a styrene acrylic, a vinyl acrylic or an acrylated ethylene vinyl acetate copolymer and is more preferably a pure acrylic. The at least one latex polymer is preferably derived from at least one acrylic monomer selected from the group consisting of acrylic acid, acrylic acid esters, methacrylic acid, and methacrylic acid esters. For example, the at least one latex polymer can be a butyl acrylate/methyl methacrylate copolymer or a 2-ethylhexyl acrylate/methyl methacrylate copolymer. Typically, the at least one latex polymer is further derived from one or more monomers selected from the group consisting of styrene, alpha-methyl styrene, vinyl chloride, acrylonitrile, methacrylonitrile, ureido methacrylate, vinyl acetate, vinyl esters of branched tertiary monocarboxylic acids, itaconic acid, crotonic acid, maleic acid, fumaric acid, ethylene, and $C_4$-$C_8$ conjugated dienes.

Latex paint formulations typically comprise additives, e.g., at least one pigment. In a preferred embodiment of the invention the latex paint formulation includes at least one pigment selected from the group consisting of TiO2, CaCO3, clay, aluminum oxide, silicon dioxide, magnesium oxide, sodium oxide, potassium oxide, talc, barytes, zinc oxide, zinc sulfite and mixtures thereof. More preferably the at least one pigment includes TiO2, calcium carbonate or clay.

In addition to the above components, the aqueous coating composition can include one or more additives selected from the group consisting of dispersants, surfactants, rheology modifiers, defoamers, thickeners, biocides, mildewcides, colorants, waxes, perfumes and co-solvents.

Compositions of the present invention may have an absence of one or more of anionic surfactant, cationic surfactant, nonionic surfactant, zwitterionic surfactant, and/or amphoteric surfactant.

These and other features and advantages of the present invention will become more readily apparent to those skilled in the art upon consideration of the following detailed description, which describe both the preferred and alternative embodiments of the present invention.

DETAILED DESCRIPTION OF THE PREFERRED EMBODIMENTS

The present invention relates to, in one embodiment, the use of a particular family of copolymers for latex dispersions, binders, paints and coatings. Described herein are aqueous compositions, for example, aqueous coating compositions. The aqueous compositions of the invention are aqueous polymer dispersions which include at least one latex polymer. Paints or other aqueous coatings of the present invention typically further include at least one pigment. In one embodiment, the latex has a Tg of less than 10° C., more typically less than 5° C., still more typically in the range from 5 to −10° C., e.g., 0° C.

As used herein, the term "alkyl" means a monovalent straight or branched saturated hydrocarbon radical, more typically, a monovalent straight or branched saturated ($C_1$-$C_{40}$) hydrocarbon radical, such as, for example, methyl, ethyl, n-propyl, isopropyl, n-butyl, isobutyl, tert-butyl, hexyl, octyl, hexadecyl, octadecyl, eicosyl, behenyl, tricontyl, and tetracontyl.

As used herein, the term "alkenyl" means an unsaturated straight or branched hydrocarbon radical, more typically an unsaturated straight, branched, ($C_2$-$C_{22}$) hydrocarbon radical, that contains one or more carbon-carbon double bonds, such as, for example, ethenyl, n-propenyl, iso-propenyl.

As used herein, the term "alkoxyl" means an oxy radical that is substituted with an alkyl group, such as for example, methoxyl, ethoxyl, propoxyl, isopropoxyl, or butoxyl, which may optionally be further substituted on one or more of the carbon atoms of the radical.

As used herein, the term "alkoxyalkyl" means an alkyl radical that is substituted with one or more alkoxy substituents, more typically a ($C_1$-$C_{22}$)alkyloxy-($C_1$-$C_6$)alkyl radical, such as methoxymethyl, and ethoxybutyl.

As used herein, terms "aqueous medium" and "aqueous media" are used herein to refer to any liquid medium of which water is a major component. Thus, the term includes water per se as well as aqueous solutions and dispersions.

As used herein, the term "aryl" means a monovalent unsaturated hydrocarbon radical containing one or more six-membered carbon rings in which the unsaturation may be represented by three conjugated double bonds, which may be substituted one or more of carbons of the ring with hydroxy, alkyl, alkoxyl, alkenyl, halo, haloalkyl, monocyclic aryl, or amino, such as, for example, phenyl, methylphenyl, methoxyphenyl, dimethylphenyl, trimethylphenyl, chlorophenyl, trichloromethylphenyl, triisobutyl phenyl, tristyrylphenyl, and aminophenyl.

As used herein, the term "arylalkyl" means an alkyl group substituted with one or more aryl groups, more typically a ($C_1$-$C_{18}$)alkyl substituted with one or more ($C_6$-$C_{14}$)aryl substituents, such as, for example, phenylmethyl, phenylethyl, and triphenylmethyl.

As used herein, the term "aryloxy" means an oxy radical substituted with an aryl group, such as for example, phenyloxy, methylphenyl oxy, isopropylmethylphenyloxy.

As used herein, the terminology "($C_x$-$C_y$)" in reference to an organic group, wherein x and y are each integers, indicates that the group may contain from x carbon atoms to y carbon atoms per group.

As used herein, the term "cycloalkenyl" means an unsaturated hydrocarbon radical, typically an unsaturated ($C_5$-$C_{22}$) hydrocarbon radical, that contains one or more cyclic alkenyl rings and which may optionally be substituted on one or more carbon atoms of the ring with one or two ($C_1$-$C_6$) alkyl groups per carbon atom, such as cyclohexenyl, cycloheptenyl, and "bicyloalkenyl" means a cycloalkenyl ring system that comprises two condensed rings, such as bicycloheptenyl.

As used herein, the term "cycloalkyl" means a saturated hydrocarbon radical, more typically a saturated ($C_5$-$C_{22}$) hydrocarbon radical, that includes one or more cyclic alkyl rings, which may optionally be substituted on one or more carbon atoms of the ring with one or two ($C_1$-$C_6$)alkyl groups per carbon atom, such as, for example, cyclopentyl, cycloheptyl, cyclooctyl, and "bicyloalkyl" means a cycloalkyl ring system that comprises two condensed rings, such as bicycloheptyl.

As used herein, an indication that a composition is "free" of a specific material means the composition contains no measurable amount of that material.

As used herein, the term "heterocyclic" means a saturated or unsaturated organic radical that comprises a ring or condensed ring system, typically comprising from 4 to 16 ring atoms per ring or ring system, wherein such ring atoms comprise carbon atoms and at least one heteroatom, such as for example, O, N, S, or P per ring or ring system, which may optionally be substituted on one or more of the ring atoms, such as, for example, thiophenyl, benzothiphenyl, thianthrenyl, pyranyl, benzofuranyl, xanthenyl, pyrolidinyl, pyrrolyl, pyradinyl, pyrazinyl, pyrimadinyl, pyridazinyl, indolyl, quinonyl, carbazolyl, phenathrolinyl, thiazolyl, oxazolyl, phenoxazinyl, or phosphabenzenyl.

As used herein, the term "hydroxyalkyl" means an alkyl radical, more typically a ($C_1$-$C_{22}$)alkyl radical, that is substituted with one or more hydroxyl groups, such as for example, hydroxymethyl, hydroxyethyl, hydroxypropyl, and hydroxydecyl.

As used herein the term "(meth)acrylate" refers collectively and alternatively to the acrylate and methacrylate and the term "(meth)acrylamide" refers collectively and alternatively to the acrylamide and methacrylamide, so that, for example, "butyl (meth)acrylate" means butyl acrylate and/or butyl methacrylate.

As used herein, "molecular weight" in reference to a polymer or any portion thereof, means to the weight-average molecular weight ("$M_w$") of the polymer or portion. $M_w$ of a polymer is a value measured by gel permeation chromatography (GPC) with an aqueous eluent or an organic eluent (for example dimethylacetamide, dimethylformamide, and the like), depending on the composition of the polymer, light scattering (DLS or alternatively MALLS), viscometry, or a number of other standard techniques. $M_w$ of a portion of a polymer is a value calculated according to known techniques from the amounts of monomers, polymers, initiators and/or transfer agents used to make the portion.

As used herein, the indication that a radical may be "optionally substituted" or "optionally further substituted" means, in general, unless further limited either explicitly or by the context of such reference, such radical may be substituted with one or more inorganic or organic substituent groups, for example, alkyl, alkenyl, aryl, arylalkyl, alkaryl, a hetero atom, or heterocyclyl, or with one or more functional groups capable of coordinating to metal ions, such as hydroxyl, carbonyl, carboxyl, amino, imino, amido, phosphonic acid, sulphonic acid, or arsenate, or inorganic and organic esters thereof, such as, for example, sulphate or phosphate, or salts thereof.

As used herein, "parts by weight" or "pbw" in reference to a named compound refers to the amount of the named compound, exclusive, for example, of any associated solvent. In some instances, the trade name of the commercial source of the compound is also given, typically in parentheses. For example, a reference to "10 pbw cocoamidopropylbetaine ("CAPB", as MIRATAINE BET C-30)" means 10 pbw of the actual betaine compound, added in the form of a commercially available aqueous solution of the betaine compound having the trade name "MIRATAINE BET C-30", and exclusive of the water contained in the aqueous solution.

As used herein, an indication that a composition is "substantially free" of a specific material, means the composition contains no more than an insubstantial amount of that material, and an "insubstantial amount" means an amount that does not measurably affect the desired properties of the composition.

As used herein, the term "surfactant" means a compound that reduces surface tension when dissolved in water.

"Surfactant effective amount" means the amount of the surfactant that provides a surfactant effect to enhance the stability of emulsions of the polymers.

I. Additive

In one embodiment, the compound of the present invention is a surfactant or characterized as a surfactant. In one embodiment, the compound of the present invention is an emulsifier or characterized as an emulsifier. In one embodiment, the compound of the present invention is a dispersant or characterized as a dispersant. In one embodiment, the compound of the present invention is an additive or characterized as an additive. In yet another embodiment, the compound of the present invention is characterized as at least one of an emulsifier, dispersant, surfactant or additive.

In one embodiment, the compound of the present invention is according to structure D.XXX:

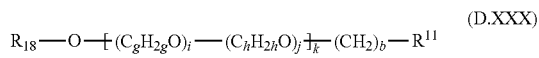
(D.XXX)

wherein:
g is an integer from 2 to 4;
h is an integer from 2 to 4;
b is an integer from 0 to 1;
k is an integer from 0 to 100;
i is an integer from 0 to 40, or from 0 to 20;
j is an integer from 0 to 40, or from 0 to 20;
$R^{18}$ is an anionic, nonionic or cationic end group;
$R^{11}$ is a tri-substituted aromatic group according to the structure D.XII

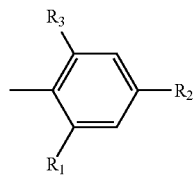
D.XII wherein $R_1$, $R_2$ and $R_3$ are independently selected from the following structures D.XIIa, D.XIIb, D.XIIc, D.XIId:

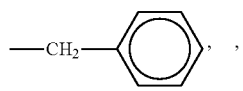
D.XIIIa

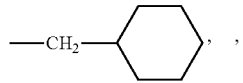
D.XIIIb

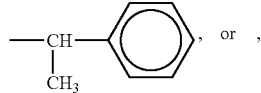
D.XIIIc
or ,

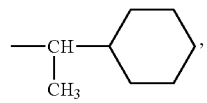
D.XIIId or a $C_2$-$C_{30}$ branched or linear alkyl group or alkenyl group; wherein at least one of $R_1$, $R_2$ and $R_3$ is the $C_2$-$C_{30}$ branched or linear alkyl group or alkenyl group and at least one of $R_1$, $R_2$ and $R_3$ is selected from structure D.XIIa, D.XIIb, D.XIIc, or D.XIId.

The $C_2$-$C_{30}$ branched or linear alkyl group or alkenyl group can be a $C_3$-$C_{14}$ branched or linear alkyl group or alkenyl group, or a $C_6$-$C_{14}$ branched or linear alkyl group or alkenyl group, or a $C_8$-$C_{12}$ branched or linear alkyl group or alkenyl group, or a $C_4$-$C_{12}$ branched or linear alkyl group or alkenyl group. Preferably, The $C_2$-$C_{30}$ branched or linear alkyl group or alkenyl group can be a $C_8$-$C_{12}$ branched or linear alkyl group or alkenyl group, or a $C_4$-$C_{12}$ branched or linear alkyl group or alkenyl group.

In one embodiment, the $C_2$-$C_{30}$ branched or linear alkyl group or alkenyl group is a $C_3$-$C_{30}$ branched or linear alkyl group or alkenyl group. In one embodiment, the $C_2$-$C_{30}$ branched or linear alkyl group or alkenyl group is a $C_4$-$C_{30}$ branched or linear alkyl group or alkenyl group. In one embodiment, the $C_2$-$C_{30}$ branched or linear alkyl group or alkenyl group is a $C_5$-$C_{30}$ branched or linear alkyl group or alkenyl group. In one embodiment, the $C_2$-$C_{30}$ branched or linear alkyl group or alkenyl group is a $C_6$-$C_{30}$ branched or linear alkyl group or alkenyl group. In one embodiment, the $C_2$-$C_{30}$ branched or linear alkyl group or alkenyl group is a $C_7$-$C_{30}$ branched or linear alkyl group or alkenyl group. In one embodiment, the $C_2$-$C_{30}$ branched or linear alkyl group or alkenyl group is a $C_8$-$C_{30}$ branched or linear alkyl group or alkenyl group. In one embodiment, the $C_2$-$C_{30}$ branched or linear alkyl group or alkenyl group is a $C_9$-$C_{30}$ branched or linear alkyl group or alkenyl group. In one embodiment, the $C_2$-$C_{30}$ branched or linear alkyl group or alkenyl group is a $C_{10}$-$C_{30}$ branched or linear alkyl group or alkenyl group.

In another embodiment, the $C_2$-$C_{30}$ branched or linear alkyl group or alkenyl group is a $C_2$-$C_{28}$ branched or linear alkyl group or alkenyl group. In one embodiment, the $C_2$-$C_{30}$ branched or linear alkyl group or alkenyl group is a $C_3$-$C_{26}$ branched or linear alkyl group or alkenyl group. In one embodiment, the $C_2$-$C_{30}$ branched or linear alkyl group or alkenyl group is a $C_4$-$C_{24}$ branched or linear alkyl group or alkenyl group. In one embodiment, the $C_2$-$C_{30}$ branched or linear alkyl group or alkenyl group is a $C_6$-$C_{24}$ branched or linear alkyl group or alkenyl group. In another embodiment, the $C_8$-$C_{24}$ branched or linear alkyl group or alkenyl group is a $C_{10}$-$C_{24}$ branched or linear alkyl group or alkenyl group.

In another embodiment, the $C_2$-$C_{30}$ branched or linear alkyl group or alkenyl group is a $C_6$-$C_{20}$ branched or linear alkyl group or alkenyl group. In another embodiment, the $C_2$-$C_{30}$ branched or linear alkyl group or alkenyl group is a $C_6$-$C_{18}$ branched or linear alkyl group or alkenyl group. In another embodiment, the $C_2$-$C_{30}$ branched or linear alkyl group or alkenyl group is a $C_8$-$C_{16}$ branched or linear alkyl group or alkenyl group.

In one embodiment, $R^{18}$ is —OH, —OCH$_3$, —OC$_2$H$_5$, —OC$_3$H$_7$, —OC$_4$H$_9$, —OC$_5$H$_{11}$, —OC$_6$H$_{13}$, —Cl, —Br, —ON, Phosphonate (—PO$_3^-$M$^+$), Phosphate (PO$_4^-$M$^+$), Sulfate (SO$_4^-$M$^+$), Sulfonate (SO$_3^-$M$^+$), carboxylate (COO$^-$M$^+$), a nonionic group, or a quaternary ammonium ion, wherein M+ is a cation including but not limited to H$^+$, Na$^+$, NH$_4^+$, K$^+$ or Li$^+$. In one embodiment, R$^{18}$ is alkyl, hydroxyalkyl, alkoxyalkyl, cycloalkyl, aryl, arylalkyl, or aryloxy. In another embodiment, R$^{18}$ is (C$_1$-C$_{22}$)alkyl, (C$_1$-C$_{22}$)hydroxyalkyl, (C$_2$-C$_{22}$)alkoxyalkyl, (C$_6$-C$_{24}$)cycloalkyl, (C$_6$-C$_{40}$)aryl, or (C$_7$-C$_{40}$)arylalkyl, more typically (C$_2$-C$_{12}$)alkyl In one embodiment, R$^{18}$ is an inorganic or organic substituent group, such as, for example, alkyl, alkenyl, aryl, aralkyl, alkaryl, a hetero atom, or heterocyclyl, or with one or more functional groups such as hydroxyl, carbonyl, carboxyl, amino, imino, amido, phosphonic acid, sulphonic acid, or inorganic and organic esters thereof, such as, for example, sulphate or phosphate, or salts thereof.

In one embodiment, the R$^{11}$ is a tri-substituted aromatic group according to the structure D.XII

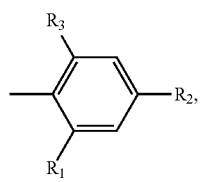

(D.XII)

wherein R$_1$, R$_2$ and R$_3$ are independently selected from:
a styryl group, or
a C$_2$-C$_{30}$ branched or linear alkyl group or alkenyl group; wherein at least one of R$_1$, R$_2$ and R$_3$ is the C$_2$-C$_{30}$ branched or linear alkyl group or alkenyl group and at least one of R$_1$, R$_2$ and R$_3$ is the styryl group.

In another embodiment, the R$^{11}$ is a tri-substituted aromatic group is according to structure D.XII-1:

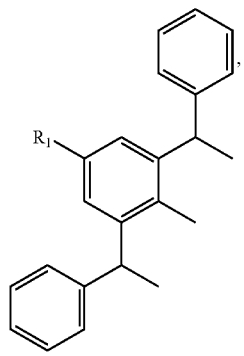

(D.XII-1)

wherein R$_1$, is the C$_2$-C$_{30}$ branched or linear alkyl group or alkenyl group In one embodiment, the emulsifier, surfactant, additive and/or disperant as described herein comprises a tri-substituted group according to structure (D.I):

R$^{18}$—R$^{14}$—R$^{13}$—R$^{12}$—R$^{11}$ (D.I).

R$^{12}$ is absent or is a bivalent linking group,
R$^{13}$ is bivalent polyether group, and
R$^{14}$ is absent or is a bivalent linking group;
R$^{11}$ is according to structure (D.XII), above;
R$^{18}$ is a nonionic, anionic, cationic or nonionic end group.

In one embodiment, R$^{18}$ is a nonionic or anionic end group.

In one embodiment, R$^{18}$ is —OH, —OCH$_3$, —OC$_2$H$_5$, —OC$_3$H$_7$, —OC$_4$H$_9$, —OC$_5$H$_{11}$, —OC$_6$H$_{13}$, —Cl, —Br, —CN, Phosphonate (—PO$_3^-$M$^+$), Phosphate (PO$_4^-$M$^+$), Sulfate (SO$_4^-$M$^+$), Sulfonate (SO$_3^-$M$^+$), carboxylate (COO$^-$M$^+$), a nonionic group, or a quaternary ammonium ion, wherein M+ is a cation including but not limited to H$^+$, Na$^+$, NH$_4^+$, K$^+$ or Li$^+$.

In one embodiment, R$^{18}$ is an inorganic or organic substituent group, such as, for example, alkyl, alkenyl, aryl, aralkyl, alkaryl, a hetero atom, or heterocyclyl, or with one or more functional groups such as hydroxyl, carbonyl, carboxyl, amino, imino, amido, phosphonic acid, sulphonic acid, or inorganic and organic esters thereof, such as, for example, sulphate or phosphate, or salts thereof.

In one embodiment, R$^{12}$ is O, a bivalent hydrocarbon group, even more typically a methylene group or chain of from 2 to 6 methylene units, or a bivalent alkyleneoxyl group, such as ethyleneoxy. In one embodiment, R$^{12}$ is according to structure (D.VIII):

—(CH$_2$)$_b$-A- (D.IX)

wherein A is O or absent, and b is an integer of from 1 to 6.

More typically, R$^{13}$ is a bivalent polyether group comprising a linear chain of from 2 to 100 units, each of which may independently be (C$_2$-C$_4$)oxyalkylene, more typically, (C$_2$-C$_3$)oxyalkylene. In one embodiment, R$^{13}$ is a bivalent polyether group comprising a chain of from 2 to 100 polymerized oxyethylene units and oxypropylene units, which may be arranged alternately, randomly, or in blocks. In one embodiment, R$^{13}$ is a bivalent polyether group comprising a block of polyoxyethylene units and a block of oxypropylene units, more typically, a block of polyoxyethylene units and a block of oxypropylene units, wherein the block of oxypropylene units is disposed between and links the block of oxyethylene units and the R$^{12}$ substituent, if present, or the R$^{11}$ substituent, if R$^{12}$ is not present.

In one embodiment, R$_{12}$ is —(CH$_2$)$_x$O—, wherein x is an integer from 1 to 20 (e.g., use of styrenated benzyl alcohols)

In another embodiment, R$_{12}$ is —CH$_2$CH(OH)CH$_2$O— or —CH$_2$CH(CH$_2$OH)O— (e.g., use of epichlorohydrin as coupling agent)

In one embodiment, R$_{13}$ is:
—[CH(R$_{20}$)CH(R$_{21}$)O]$_x$— wherein x is an integer of from 0 to 100, and R$_{20}$ and R$_{21}$ are independently selected from any of the following:
H; —CH$_2$OH; phenyl; —CH$_2$Cl;
a C$_1$-C$_{30}$ straight or branched alkyl or alkenyl;
—CH$_2$OR$_{22}$ wherein R$_{22}$ is C$_1$-C$_{30}$ straight or branched alkyl or alkenyl, phenyl, or alkyl substituted phenyl; or
R'COOCH$_2$— where R' is C$_1$-C$_{30}$ straight or branched alkyl or alkenyl.

In one embodiment, R$^{13}$ is according to structure (D.X):

—[(C$_g$H$_{2g}$O)$_i$—(C$_h$H$_{2h}$O)$_j$]$_k$— (D.X)

wherein:
g and h are independently integers of from 2 to 5, more typically 2 or 3,
each i is independently an integer of from 1 to about 80, more typically from 1 to about 50,
each j is independently an integer of from 0 to about 80, more typically from 1 to about 50,
k is an integer of from 1 to about 50, provided that the product obtained by multiplying the integer k times the sum of i+j is from 2 to about 100.

In another embodiment k is an integer having a lower limit of 0. In another embodiment k is an integer having a lower limit of 1. In another embodiment k is an integer having a lower limit of 3. In another embodiment k is an integer having a lower limit of 5. In another embodiment k is an integer having a lower limit of 8. In another embodiment k is an integer having a lower limit of 10. In another embodiment k is an integer having an upper limit of 100. In another embodiment k is an integer having an upper limit of 75. In another embodiment k is an integer having an upper limit of 50. In another embodiment k is an integer having an upper limit of 40. In another embodiment k is an integer having an upper limit of 60. In another embodiment k is an integer having an upper limit of 25. In another embodiment k is an integer having an upper limit of 35.

In another embodiment, if i≠0, j≠0, and g≠h, the respective —($C_pH_{2p}O$)— and (—$C_qH_{2q}O$)— oxylakylene units may be arranged randomly, in blocks, or in alternating order.

In one embodiment, g=2, h=3, i is an integer of from 1 to 50, more typically 10 to 40, and even more typically from 15 to about 30, j is an integer of from 1 to 30, more typically from 2 to 20, and even more typically from about 2 to about 10, and k=1.

In one embodiment, $R^{14}$ is O, —$(CH_2)_n$—O—, or is according to structure (D.XI):

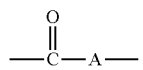

(D.XI)

wherein:

n is an integer of from 1 to 6,

A is O or $NR^{17}$, and $R^{17}$ is H or ($C_1$-$C_4$)alkyl.

In another embodiment of structure (D.I) $R^{11}$ is a tri-styryl group according to the following structure D.XII.

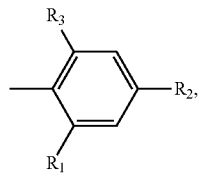

D.XII wherein $R_1$, $R_2$ and $R_3$ are independently selected from the following structures:

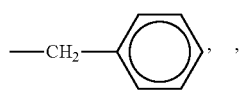

D.XIIIa

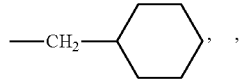

D.XIIIb

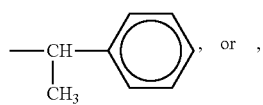

D.XIIIc

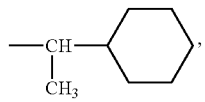

D.XIIId or a $C_2$-$C_{30}$ branched or linear alkyl group or alkenyl group.

In one embodiment, at least one of $R_1$, $R_2$ and $R_3$ is the $C_2$-$C_{30}$ branched or linear alkyl group or alkenyl group and at least one of $R_1$, $R_2$ and $R_3$ is selected from structure D.XIIa, D.XIIb, D.XIIc, or D.XIId.

In another embodiment, $R^{11}$ is a tri-styryl group according to the above-discussed structure D.XII.

and $R^{19}$, b, g, h, i, j, and k are each as defined above, namely:

$R^{19}$ is H or ($C_1$-$C_4$)alkyl, b is an integer of from 1 to 6, g and h are independently integers of from 2 to 5, more typically 2 or 3, each i is independently an integer of from 1 to about 80, more typically from 1 to about 50, each j is independently an integer of from 0 to about 80, more typically from 1 to about 50, k is an integer of from 1 to about 50, provided that the product obtained by multiplying the integer k times the sum of i+j is from 2 to about 100.

In another embodiment k is an integer having a lower limit of 0. In another embodiment k is an integer having a lower limit of 1. In another embodiment k is an integer having a lower limit of 3. In another embodiment k is an integer having a lower limit of 5. In another embodiment k is an integer having a lower limit of 8. In another embodiment k is an integer having a lower limit of 10. In another embodiment k is an integer having an upper limit of 100. In another embodiment k is an integer having an upper limit of 75. In another embodiment k is an integer having an upper limit of 50. In another embodiment k is an integer having an upper limit of 40. In another embodiment k is an integer having an upper limit of 60. In another embodiment k is an integer having an upper limit of 25. In another embodiment k is an integer having an upper limit of 35.

Applications

When surface active alkoxylated tri-substituted aromatic compound is employed as an emulsifier in emulsion polymerization to form the latex polymer, the latex polymer is made from a mixture wherein the surface active emulsifier utilized is. In one embodiment, the emulsifier is added in an amount greater than 1% by weight of the polymer or monomers used to form the latex polymer. In one embodiment, the emulsifier is added in an amount greater than 1.3% by weight of the polymer or monomers used to form the latex polymer, in an amount greater than 1.6% by weight of the polymer or monomers used to form the latex polymer, typically in an amount greater than about 2% by weight of the polymer or monomers used to form the latex polymer, more typically in an amount greater than about 4% by weight of the polymer or monomers used to form the latex polymer, and most typically in an amount greater than about 7.5% by weight of the polymer or monomers used to form the latex polymer. In another embodiment, the latex coating composition contains an emulsifier in an amount greater than about 8% by weight of the polymer or monomers used to form the latex polymer, or greater than about 10% by weight of the polymer or monomers. In another embodiment, the emulsifier is added is between about 1.6% and 7.5% by weight of the polymer or monomers used to form the latex polymer. In another embodiment, emulsifier added is between about 1.6% and 45% by weight of the polymer or monomers used to form the latex polymer, typically between about 1.6% and 35% by weight of the polymer or monomers used to form the latex polymer In another embodiment the compounds as described herein can be used as an additive to an already formed aqueous dispersion of latex polymer.

In some embodiments, the additive is a freeze-thaw additive that can be added any point in the production of the aqueous coating composition, including but not limited to during the emulsification step, during formulation, etc. It is also understood that the freeze-thaw additive can be post-added to the aqueous coating composition or a concentrate thereof.

This results in an aqueous composition comprising the surface active alkoxylated compound and the latex polymer. When the surface active alkoxylated compound is employed as an additive to an already formed aqueous latex dispersion, the resulting composition has alkoxylated compound additive in an amount of about 1 to 10, Typically 2 to 8 or 2 to 6, parts per 100 parts by weight of monomers used to form the latex polymer.

In another embodiment the above-described surface active compound of any of the structural formulas above can be used as an additive to an during formulation of paint or aqueous coating composition. Formulation is the stage at which additives are added to a base aqueous latex polymer dispersion to make it into final product such as a paint or coating. When the surface active alkoxylated compound is employed as an additive to an already formed paint or aqueous coating composition, e.g., aqueous latex coating dispersion, the resulting composition has alkoxylated compound additive typically in an amount greater than about 1.3% by weight of the polymer or monomers used to form the latex polymer, more typically in an amount greater than about 1.6% by weight of the polymer or monomers used to form the latex polymer, yet more typically in an amount greater than about 2% by weight of the polymer or monomers used to form the latex polymer, even more typically in an amount greater than about 4% by weight of the polymer or monomers used to form the latex polymer, and most typically in an amount greater than about 7.5% by weight of the polymer or monomers used to form the latex polymer. In another embodiment, the latex coating composition contains surface active alkoxylated compound in an amount between about 1.6% and 7.5% by weight of the polymer or monomers used to form the latex polymer. In another embodiment, the latex coating composition contains surface active alkoxylated compound in an amount between about 1.6% and 45% by weight of the polymer or monomers used to form the latex polymer, typically between about 1.6% and 35%. Pigment is a typical additive, for example, added during formulation of paint from raw aqueous latex polymer dispersion.

The aqueous coating compositions of the present invention are freeze-thaw stable where the freeze-thaw additive is present in the aqueous coating composition in the amounts by weight of the polymer as described above, where the polymer can have a Tg of between about $-15°$ C. and about $12°$ C. and a mean particle size of less than about 200 nm, or a Tg of between about $-5°$ C. and about $5°$ C. and a mean particle size of less than about 200 nm, or a Tg of between about $-5°$ C. and about $0°$ C. and a mean particle size of less than about 200 nm, or a Tg of between about $-15°$ C. and about $12°$ C. and a mean particle size of less than about 190 nm, or a Tg of between about $-5°$ C. and about $5°$ C. and a mean particle size of less than about 190 nm, or a Tg of between about $-5°$ C. and about $0°$ C. and a mean particle size of less than about 190 nm, or a Tg of between about $-15°$ C. and about $12°$ C. and a mean particle size of less than about 175 nm, or a Tg of between about $-5°$ C. and about $5°$ C. and a mean particle size of less than about 175 nm, or a Tg of between about $-5°$ C. and about $0°$ C. and a mean particle size of less than about 175 nm. As described above, the mean particle size is typically between about 75 nm to about 400 nm. The aqueous coating composition can be characterized by an open time of greater than about 2 minutes, an open time of greater than about 4 minutes, an open time of greater than about 6 minutes or an open time of greater than about 12 minutes.

The present invention further includes a method of preparing a paint or aqueous coating composition, comprising adding the at least one surface active alkoxylated compound of any of the structural formulas above during formulation of paint or aqueous coating composition comprising at least one pigment and other additives to produce the final paint or aqueous coating composition. The addition of the surface active alkoxylated compound surfactant (emulsifier) during formulation of paint or aqueous coating composition forms a coating composition having a lower VOC content while maintaining the freeze-thaw stability of the aqueous coating composition at desirable levels.

As mentioned above, the aqueous coating composition in some embodiments can include less than 2.0% of anti-freeze agents based on the total weight of the aqueous coating composition. Exemplary anti-freeze agents include ethylene glycol, diethylene glycol, propylene glycol, glycerol (1,2,3-trihydroxypropane), ethanol, methanol, 1-methoxy-2-propanol, 2-amino-2-methyl-1-propanol, and FTS-365 (a freeze-thaw stabilizer from Inovachem Specialty Chemicals). More typically, the aqueous coating composition includes less than 1.0% or is substantially free (e.g. includes less than 0.1%) of anti-freeze agents. Accordingly, the aqueous coating composition of the invention typically has a VOC level of less than about 100 g/L and more typically less than or equal to about 50 g/L. Despite the fact that the aqueous coating compositions of the invention include little or no anti-freeze agents, the compositions possess freeze-thaw stabilities at levels desirable in the art.

For example, the aqueous coating compositions of the invention can be subjected to freeze-thaw cycles using ASTM method D2243-82 or ASTM D2243-95 without coagulation.

The balance of the aqueous coating composition of the invention is water. Although much of the water is present in the polymer latex dispersion and in other components of the aqueous coating composition, water is generally also added separately to the aqueous coating composition. Typically, the aqueous coating composition includes from about 10% to about 85% by weight and more typically from about 35% to about 80% by weight water. Stated differently, the total solids content of the aqueous coating composition is typically from about 15% to about 90%, more typically, from about 20% to about 65%.

Latex paints and coatings may contain various adjuvants, such as pigments, fillers and extenders. Useful pigments include, but are not limited to, titanium dioxide, mica, and iron oxides. Useful fillers and extenders include, but are not limited to, barium sulfate, calcium carbonate, clays, talc, and silica. The compositions of the present invention described herein are compatible with most latex paint systems and provide highly effective and efficient thickening.

In formulating latexes and latex paints/coatings, physical properties that may be considered include, but are not limited to, viscosity versus shear rate, ease of application to surface, spreadability, and shear thinning.

Emulsion polymerization is discussed in G. Pohlein, "Emulsion Polymerization", Encyclopedia of Polymer Science and Engineering, vol. 6, pp. 1-51 (John Wiley & Sons, Inc., NY, N.Y., 1986), the disclosure of which is incorporated herein by reference. Emulsion polymerization is a heterogeneous reaction process in which unsaturated monomers or monomer solutions are dispersed in a continuous phase with the aid of an emulsifier system and polymerized with free-radical or redox initiators. The product, a colloidal dispersion of the polymer or polymer solution, is called a latex.

The monomers typically employed in emulsion polymerization to make latex for latex paint include such monomers as methyl acrylate, ethyl acrylate, methyl methacrylate, butyl acrylate, 2-ethyl hexyl acrylate, other acrylates, methacrylates and their blends, acrylic acid, methacrylic acid, styrene, vinyl toluene, vinyl acetate, vinyl esters of higher carboxylic acids than acetic acid, e.g. vinyl versatate, acrylonitrile, acrylamide, butadiene, ethylene, vinyl chloride and the like, and mixtures thereof. This is further discussed below in the section entitled "Latex Monomers".

In the above process, suitable initiators, reducing agents, catalysts and surfactants are well known in the art of emulsion polymerization. Typical initiators include ammonium persulfate (APS), hydrogen peroxide, sodium, potassium or ammonium peroxydisulfate, dibenzoyl peroxide, lauryl peroxide, ditertiary butyl peroxide, 2,2'-azobisisobutyronitrile, t-butyl hydroperoxide, benzoyl peroxide, and the like. Commonly used redox initiation systems are described e.g., by A. S. Sarac in Progress in Polymer Science 24(1999), 1149-1204.

Suitable reducing agents are those which increase the rate of polymerization and include for example, sodium bisulfite, sodium hydrosulfite, sodium formaldehyde sulfoxylate, ascorbic acid, isoascorbic acid, and mixtures thereof.

Suitable catalysts are those compounds which increase the rate of polymerization and which, in combination with the above-described reducing agents, promote decomposition of the polymerization initiator under the reaction conditions. Suitable catalysts include transition metal compounds such as, for example, ferrous sulfate heptahydrate, ferrous chloride, cupric sulfate, cupric chloride, cobalt acetate, cobaltous sulfate, and mixtures thereof.

Emulsion polymerization occurs in the presence of an emulsifier. Typically the mixture contains 0.01 to 6 wt % (or in other embodiment 0.05 to 6 wt %) emulsifier based on weight of latex monomers.

Aside from the compounds as described herein, typical emulsifiers are ionic or non-ionic surfactants polymerizable or non-polymerizable in the aqueous coating composition including latex polymer. Suitable ionic and nonionic surfactants are alkyl polyglycol ethers such as ethoxylation products of lauryl, tridecyl, oleyl, and stearyl alcohols; alkyl phenol polyglycol ethers such as ethoxylation products of octyl- or nonylphenol, diisopropyl phenol, triisopropyl phenol; alkali metal or ammonium salts of alkyl, aryl or alkylaryl sulfonates, sulfates, phosphates, and the like, including sodium lauryl sulfate, sodium octylphenol glycolether sulfate, sodium dodecylbenzene sulfonate, sodium lauryldiglycol sulfate, and ammonium tritertiarybutyl phenol and penta- and octa-glycol sulfonates, sulfosuccinate salts such as disodium ethoxylated nonylphenol half ester of sulfosuccinic acid, disodium n-octyldecyl sulfosuccinate, sodium dioctyl sulfosuccinate, and the like.

The polymer latex binder can be produced by first preparing an initiator solution comprising the initiator and water. A monomer pre-emulsion is also prepared comprising one or more surfactants (emulsifiers), and other latex monomers to be used to form the latex polymer, water, and additional additives such as NaOH.

Thus, a typical process of emulsion polymerization preferably involves charging water to a reactor and feeding as separate streams a pre-emulsion of the monomer and a solution of the initiator. In particular, the polymer latex binder can be prepared using emulsion polymerization by feeding the monomers used to form the latex binder to a reactor in the presence of at least one initiator and at least one surfactant and polymerizing the monomers to produce the latex binder. Typically the initiator solution and monomer pre-emulsion are continuously added to the reactor over a predetermined period of time (e.g. 1.5-5 hours) to cause polymerization of latex monomers to produce the latex polymer.

Prior to the addition of the initiator solution and the monomer pre-emulsion, a seed latex such as a polystyrene seed latex can be added to the reactor. For example, a small amount of the pre-emulsion and a portion of the initiator may be charged initially at the reaction temperature to produce "seed" latex. The "seed" latex procedure results in better particle-size reproducibility.

Under "normal" initiation conditions, that is initiation conditions under which the initiator is activated by heat, the polymerization is normally carried out at about 60-90° C. A typical "normal" initiated process, for example, could employ ammonium persulfate as initiator at a reaction temperature of 80+/−2° C. Under "redox" initiation conditions, namely initiation conditions under which the initiator is activated by a reducing agent, the polymerization is normally carried out at 60-70° C. Normally, the reducing agent is added as a separate solution. A typical "redox" initiated process, for example, could employ potassium persulfate as the initiator and sodium metabisulfite as the reducing agent at a reaction temperature of 65+/−2° C.

The reactor is operated at desired reaction temperature at least until all the monomers are fed to produce the polymer latex binder. Once the polymer latex binder is prepared, it is preferably chemically stripped thereby decreasing its residual monomer content. Preferably, it is chemically stripped by continuously adding an oxidant such as a peroxide (e.g. t-butylhydroperoxide) and a reducing agent (e.g. sodium acetone bisulfite), or another redox pair such as those described by A. S. Sarac in Progress in Polymer Science 24(1999), 1149-1204, to the latex binder at an elevated temperature and for a predetermined period of time (e.g. 0.5 hours). The pH of the latex binder can then be adjusted and other additives added after the chemical stripping step.

In the above emulsions, the polymer preferably exists as a generally spherical particle, dispersed in water, with a diameter of about 50 nanometers to about 500 nanometers.

For purposes of this description, monomers from which latex polymers may be derived are termed "latex monomers".

The latex monomers fed to a reactor to prepare the polymer latex binder preferably include at least one acrylic monomer selected from the group consisting of acrylic acid, acrylic acid esters, methacrylic acid, and methacrylic acid esters. In addition, the monomers can include styrene, vinyl acetate, or ethylene. The monomers can also include one or more monomers selected from the group consisting of styrene, (alpha)-methyl styrene, vinyl chloride, acrylonitrile, methacrylonitrile, ureido methacrylate, vinyl acetate, vinyl esters of branched tertiary monocarboxylic acids (e.g. vinyl esters commercially available under the mark VEOVA from Shell Chemical Company or sold as EXXAR neo vinyl esters by ExxonMobil Chemical Company), itaconic acid, crotonic acid, maleic acid, fumaric acid, and ethylene. It is also possible to include C4-C8 conjugated dienes such as 1,3-butadiene, isoprene or chloroprene. Commonly used monomers in making acrylic paints are butyl acrylate, methyl methacrylate, ethyl acrylate and the like. Preferably, the monomers include one or more monomers selected from the group consisting of n-butyl acrylate, methyl methacrylate, styrene and 2-ethylhexyl acrylate.

The latex polymer is typically selected from the group consisting of pure acrylics (comprising acrylic acid, methacrylic acid, an acrylate ester, and/or a methacrylate ester as the main monomers); styrene acrylics (comprising styrene and acrylic acid, methacrylic acid, an acrylate ester, and/or a methacrylate ester as the main monomers); vinyl acrylics (comprising vinyl acetate and acrylic acid, methacrylic acid, an acrylate ester, and/or a methacrylate ester as the main monomers); and acrylated ethylene vinyl acetate copolymers (comprising ethylene, vinyl acetate and acrylic acid, methacrylic acid, an acrylate ester, and/or a methacrylate ester as the main monomers). The monomers can also include other main monomers such as acrylamide and acrylonitrile, and one or more functional monomers such as itaconic acid and ureido methacrylate, as would be readily understood by those skilled in the art. In a particularly preferred embodiment, the latex polymer is a pure acrylic such as a butyl acrylate/methyl methacrylate copolymer derived from monomers including butyl acrylate and methyl methacrylate.

In typical acrylic paint compositions the polymer is comprised of one or more esters of acrylic or methacrylic acid, typically a mixture, e.g. about 50/50 by weight, of a high $T_g$ monomer (e.g. methyl methacrylate) and a low $T_g$ monomer (e.g. butyl acrylate), with small proportions, e.g. about 0.5% to about 2% by weight, of acrylic or methacrylic acid. The vinyl-acrylic paints usually include vinyl acetate and butyl acrylate and/or 2-ethyl hexyl acrylate and/or vinyl versatate. In vinyl-acrylic paint compositions, at least 50% of the polymer formed is comprised of vinyl acetate, with the remainder being selected from the esters of acrylic or methacrylic acid. The styrene/acrylic polymers are typically similar to the acrylic polymers, with styrene substituted for all or a portion of the methacrylate monomer thereof.

The latex polymer dispersion preferably includes from about 30 to about 75% solids and a mean latex particle size of from about 70 to about 650 nm. The latex polymer is preferably present in the aqueous coating composition in an amount from about 5 to about 60 percent by weight, and more preferably from about 8 to about 40 percent by weight (i.e. the weight percentage of the dry latex polymer based on the total weight of the coating composition).

The aqueous coating composition is a stable fluid that can be applied to a wide variety of materials such as, for example, paper, wood, concrete, metal, glass, ceramics, plastics, plaster, and roofing substrates such as asphaltic coatings, roofing felts, foamed polyurethane insulation; or to previously painted, primed, undercoated, worn, or weathered substrates. The aqueous coating composition of the invention can be applied to the materials by a variety of techniques well known in the art such as, for example, brush, rollers, mops, air-assisted or airless spray, electrostatic spray, and the like.

Liquid Carrier

In one embodiment, the composition of the present invention comprises the selected polymer and a liquid carrier.

In one embodiment, the liquid carrier is an aqueous carrier comprising water and the treatment solution is in the form of a solution, emulsion, or dispersion of the material and additives. In one embodiment, the liquid carrier comprises water and a water miscible organic liquid. Suitable water miscible organic liquids include saturated or unsaturated monohydric alcohols and polyhydric alcohols, such as, for example, methanol, ethanol, isopropanol, cetyl alcohol, benzyl alcohol, oleyl alcohol, 2-butoxyethanol, and ethylene glycol, as well as alkylether diols, such as, for example, ethylene glycol monoethyl ether, propylene glycol monoethyl ether and diethylene glycol monomethyl ether.

As used herein, terms "aqueous medium" and "aqueous media" are used herein to refer to any liquid medium of which water is a major component. Thus, the term includes water per se as well as aqueous solutions and dispersions.

VI. Other Additives

As described above, latex paints and coatings may contain various adjuvants.

The aqueous coating compositions of the invention include less than 2% by weight and preferably less than 1.0% by weight of anti-freeze agents based on the total weight of the aqueous coating composition. For example, the aqueous coating compositions may be substantially free of anti-freeze agents.

The aqueous coating composition typically includes at least one pigment. The term "pigment" as used herein includes non-film-forming solids such as pigments, extenders, and fillers. The at least one pigment is preferably selected from the group consisting of $TiO_2$ (in both anastase and rutile forms), clay (aluminum silicate), $CaCO_3$ (in both ground and precipitated forms), aluminum oxide, silicon dioxide, magnesium oxide, talc (magnesium silicate), barytes (barium sulfate), zinc oxide, zinc sulfite, sodium oxide, potassium oxide and mixtures thereof. Suitable mixtures include blends of metal oxides such as those sold under the marks MINEX (oxides of silicon, aluminum, sodium and potassium commercially available from Unimin Specialty Minerals), CELITES (aluminum oxide and silicon dioxide commercially available from Celite Company), ATOMITES (commercially available from English China Clay International), and ATTAGELS (commercially available from Engelhard). More preferably, the at least one pigment includes $TiO_2$, $CaCO_3$ or clay. Generally, the mean particle sizes of the pigments range from about 0.01 to about 50 microns. For example, the $TiO_2$ particles used in the aqueous coating composition typically have a mean particle size of from about 0.15 to about 0.40 microns. The pigment can be added to the aqueous coating composition as a powder or in slurry form. The pigment is preferably present in the aqueous coating composition in an amount from about 5 to about 50 percent by weight, more preferably from about 10 to about 40 percent by weight.

The coating composition can optionally contain additives such as one or more film-forming aids or coalescing agents. Suitable firm-forming aids or coalescing agents include plasticizers and drying retarders such as high boiling point polar solvents. Other conventional coating additives such as, for example, dispersants, additional surfactants (i.e. wetting agents), rheology modifiers, defoamers, thickeners, additional biocides, additional mildewcides, colorants such as colored pigments and dyes, waxes, perfumes, co-solvents, and the like, can also be used in accordance with the invention. For example, non-ionic and/or ionic (e.g. anionic or cationic) surfactants can be used to produce the polymer latex. These additives are typically present in the aqueous coating composition in an amount from 0 to about 15% by weight, more preferably from about 1 to about 10% by weight based on the total weight of the coating composition.

The aqueous coating composition typically includes less than 10.0% of anti-freeze agents based on the total weight of the aqueous coating composition. Exemplary anti-freeze agents include ethylene glycol, diethylene glycol, propylene glycol, glycerol (1,2,3-trihydroxypropane), ethanol, methanol, 1-methoxy-2-propanol, 2-amino-2-methyl-1-propanol, and FTS-365 (a freeze-thaw stabilizer from Inovachem Specialty Chemicals). More preferably, the aqueous coating composition includes less than 5.0% or is substantially free (e.g. includes less than 0.1%) of anti-freeze agents. Accordingly, the aqueous coating composition of the invention preferably has a VOC level of less than about 100 g/L and more preferably less than or equal to about 50 g/L.

The balance of the aqueous coating composition of the invention is water. Although much of the water is present in the polymer latex dispersion and in other components of the aqueous coating composition, water is generally also added separately to the aqueous coating composition. Typically, the aqueous coating composition includes from about 10% to about 85% by weight and more preferably from about 35% to about 80% by weight water. Stated differently, the total solids content of the aqueous coating composition is typically from about 15% to about 90%, more preferably, from about 20% to about 65%.

The coating compositions are typically formulated such that the dried coatings comprise at least 10% by volume of dry polymer solids, and additionally 5 to 90% by volume of non-polymeric solids in the form of pigments. The dried coatings can also include additives such as plasticizers, dispersants, surfactants, rheology modifiers, defoamers, thickeners, additional biocides, additional mildewcides, colorants, waxes, and the like, that do not evaporate upon drying of the coating composition.

VIII. Personal Care

The compounds of the present invention can be suitable in the preparation of personal care (cosmetics, toiletries, health and beauty aids, cosmeceuticals) and topical health care products, including without limitation, hair care products, such as shampoos (including combination shampoos, such as "two-in-one" conditioning shampoos); post-shampoo rinses; setting and style maintenance agents including setting aids, such as gels and sprays, grooming aids, such as pomades, conditioners, perms, relaxers, hair smoothing products, and the like; skin care products (facial, body, hands, scalp and feet), such as creams, lotions, conditioners, and cleansing products; anti-acne products; anti-aging products (exfoliant, keratolytic, anticellulite, antiwrinkle, and the like); skin protectants such as sunscreens, sunblock, barrier creams, oils, silicones, and the like; skin color products (whiteners, lighteners, sunless tanning accelerators, and the like); hair colorants (hair dyes, hair color rinses, highlighters, bleaches and the like); pigmented skin colorants (face and body makeups, foundation creams, mascara, rouge, lip products, and the like); bath and shower products (body cleansers, body wash, shower gel, liquid soap, soap bars, syndet bars, conditioning liquid bath oil, bubble bath, bath powders, and the like); nail care products (polishes, polish removers, strengtheners, lengtheners, hardeners, cuticle removers, softeners, and the like); and any aqueous acidic to basic composition to which an effective amount of the hydrophobic polymer can be incorporated for achieving a beneficial or desirable, physical or chemical, effect therein during storage and/or usage.

In one embodiment, the present invention is directed to a personal care composition comprising water, one or more surfactants, and the compound(s) according to the present invention.

Suitable surfactants include anionic surfactants, cationic surfactants, non-ionic surfactants, zwitterionic surfactants, and mixtures thereof.

Suitable anionic surfactants are known compounds and include, for example, linear alkylbenzene sulfonates, alpha olefin sulfonates, paraffin sulfonates, alkyl ester sulfonates, alkyl sulfates, alkyl alkoxy sulfates, alkyl sulfonates, alkyl alkoxy carboxylates, alkyl alkoxylated sulfates, monoalkyl phosphates, dialkyl phosphates, sarcosinates, isethionates, and taurates, as well as mixtures thereof, such as for example, ammonium lauryl sulfate, ammonium laureth sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium trideceth sulfate, sodium tridecyl sulfate, ammonium trideceth sulfate, ammonium tridecyl sulfate, sodium cocoyl isethionate, disodium laureth sulfosuccinate, sodium methyl oleoyl taurate, sodium laureth carboxylate, sodium trideceth carboxylate, sodium monoalkyl phosphate, sodium dialkyl phosphate, sodium lauryl sarcosinate, lauroyl sarcosine, cocoyl sarcosinate, ammonium cocyl sulfate, sodium cocyl sulfate, potassium cocyl sulfate, monoethanolamine cocyl sulfate, sodium tridecyl benzene sulfonate, sodium dodecyl benzene sulfonate, and mixtures thereof.

The cationic counterion of the anionic surfactant is typically a sodium cation but may alternatively be a potassium, lithium, calcium, magnesium, ammonium cation, or an alkyl ammonium anion having up to 6 aliphatic carbon atoms, such as anisopropylammonium, monoethanolammonium, diethanolammonium, or triethanolammonium cation. Ammonium and ethanolammonium salts are generally more soluble than the sodium salts. Mixtures of the above cations may be used.

Suitable cationic surfactants are known compounds and include, for example, mono-cationic surfactants according to structure (XX) below:

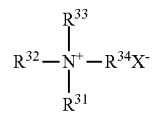

XX wherein:

R31, R32, R33 and R34 are independently hydrogen or an organic group, provided that at least one of R31, R32, R33 and R34 is not hydrogen, and X⁻ is an anion, as well as mixtures of such compounds If one to three of the R31, R32, R33 and R34 groups are each hydrogen, then the compound may be referred to as an amine salt. Some examples of cationic amine salts include polyethoxylated (2) oleyl/stearyl amine, ethoxylated tallow amine, cocoalkylamine, oleylamine, and tallow alkyl amine.

For quaternary ammonium compounds (generally referred to as quats) R31, R32, R33 and R34 may be the same or different organic group, but may not be hydrogen. In one embodiment, R31, R32, R33 and R34 are each C8-C24 branched or linear hydrocarbon groups which may comprise additional functionality such as, for example, fatty acids or derivatives thereof, including esters of fatty acids and fatty acids with alkoxylated groups; alkyl amido groups; aromatic rings; heterocyclic rings; phosphate groups; epoxy groups; and hydroxyl groups. The nitrogen atom may also be part of a heterocyclic or aromatic ring system, e.g., cetethyl morpholinium ethosulfate or steapyrium chloride.

Examples of quaternary ammonium compounds of the monoalkyl amine derivative type include: cetyl trimethyl ammonium bromide (also known as CETAB or cetrimonium bromide), cetyl trimethyl ammonium chloride (also known as cetrimonium chloride), myristyl trimethyl ammonium bromide (also known as myrtrimonium bromide or Quaternium-13), stearyl dimethyl benzyl ammonium chloride (also known as stearalkonium chloride), oleyl dimethyl benzyl ammonium chloride, (also known as olealkonium chloride), lauryl/myristryl trimethyl ammonium methosulfate (also known as cocotrimonium methosulfate), cetyl dimethyl (2)hydroxyethyl ammonium dihydrogen phosphate (also known as hydroxyethyl cetyldimonium phosphate), babassuamidopropalkonium chloride, cocotrimonium chloride, distearyldimonium chloride, wheat germ-amidopropalkonium chloride, stearyl octyldimonium methosulfate, isostearaminopropalkonium chloride, dihydroxypropyl PEG-5 linoleaminium chloride, PEG-2 stearmonium chloride, Quaternium 18, Quaternium 80, Quaternium 82, Quaternium 84, behentrimonium chloride, dicetyl dimonium chloride, behentrimonium methosulfate, tallow trimonium chloride and behenamidopropyl ethyl dimonium ethosulfate.

Quaternary ammonium compounds of the dialkyl amine derivative type include, for example, distearyldimonium chloride, dicetyl dimonium chloride, stearyl octyldimonium methosulfate, dihydrogenated palmoylethyl hydroxyethylmonium methosulfate, dipalmitoylethyl hydroxyethylmonium methosulfate, dioleoylethyl hydroxyethylmonium methosulfate, hydroxypropyl bisstearyldimonium chloride, and mixtures thereof.

Quaternary ammonium compounds of the imidazoline derivative type include, for example, isostearyl benzylimidonium chloride, cocoyl benzyl hydroxyethyl imidazolinium chloride, cocoyl hydroxyethylimidazolinium PG-chloride phosphate, Quaternium 32, and stearyl hydroxyethylimidonium chloride, and mixtures thereof.

Typical cationic surfactants comprise dialkyl derivatives such as dicetyl dimonium chloride and distearyldimonium chloride; branched and/or unsaturated cationic surfactants such as isostearylaminopropalkonium chloride or olealkonium chloride; long chain cationic surfactants such as stearalkonium chloride and behentrimonium chloride; as well as mixtures thereof.

Suitable anionic counterions for the cationic surfactant include, for example, chloride, bromide, methosulfate, ethosulfate, lactate, saccharinate, acetate and phosphate anions.

Suitable nonionic surfactants are known compounds and include amine oxides, fatty alcohols, alkoxylated alcohols, fatty acids, fatty acid esters, and alkanolamides. Suitable amine oxides comprise, (C10-C24) saturated or unsaturated branched or straight chain alkyl dimethyl oxides or alkyl amidopropyl amine oxides, such as for example, lauramine oxide, cocamine oxide, stearamine oxide, stearamidopropylamine oxide, palmitamidopropylamine oxide, decylamine oxide as well as mixtures thereof. Suitable fatty alcohols include, for example, (C10-C24) saturated or unsaturated branched or straight chain alcohols, more typically (C10-C20) saturated or unsaturated branched or straight chain alcohols, such as for example, decyl alcohol, lauryl alcohol, myristyl alcohol, cetyl alcohol, stearyl alcohol, oleyl alcohol, linoleyl alcohol and linolenyl alcohol, and mixtures thereof. Suitable alkoxylated alcohols include alkoxylated, typically ethoxylated, derivatives of (C10-C24) saturated or unsaturated branched or straight chain alcohols, more typically (C10-C20) saturated or unsaturated branched or straight chain alcohols, which may include, on average, from 1 to 22 alkoxyl units per molecule of alkoxylated alcohol, such as, for example, ethoxylated lauryl alcohol having an average of 5 ethylene oxide units per molecule. Mixtures of these alkoxylated alcohols may be used. Suitable fatty acids include (C10-C24) saturated or unsaturated carboxylic acids, more typically (C10-C22) saturated or unsaturated carboxylic acids, such as, for example, lauric acid, oleic acid, stearic acid, myristic acid, cetearic acid, isostearic acid, linoleic acid, linolenic acid, ricinoleic acid, elaidic acid, arichidonic acid, myristoleic acid, and palmitoleic acid, as well as neutralized versions thereof. Suitable fatty acid esters include esters of (C10-C24) saturated or unsaturated carboxylic acids, more typically (C10-C22) saturated or unsaturated carboxylic acids, for example, propylene glycol isostearate, propylene glycol oleate, glyceryl isostearate, and glyceryl oleate, and mixtures thereof. Suitable alkanolamides include aliphatic acid alkanolamides, such as cocamide MEA (coco monoethanolamide) and cocamide MIPA (coco monoisopropanolamide), as well as alkoxylated alkanolamides, and mixtures thereof.

Suitable amphoteric surfactants are known compounds and include for example, derivatives of aliphatic secondary and tertiary amines in which the aliphatic radical can be straight chain or branched and wherein one of the aliphatic substituents contains from about 8 to about 18 carbon atoms and one contains an anionic water-solubilizing group as well as mixtures thereof. Specific examples of suitable amphoteric surfactants include the alkali metal, alkaline earth metal, ammonium or substituted ammonium salts of alkyl amphocarboxy glycinates and alkyl amphocarboxypropionates, alkyl amphodipropionates, alkyl amphodiacetates, alkyl amphoglycinates, and alkyl amphopropionates, as well as alkyl iminopropionates, alkyl iminodipropionates, and alkyl amphopropylsulfonates, such as for example, cocoamphoacetate cocoamphopropionate, cocoamphodiacetate, lauroamphoacetate, lauroamphodiacetate, lauroamphodipropionate, lauroamphodiacetate, cocoamphopropyl sulfonate caproamphodiacetate, caproamphoacetate, caproamphodipropionate, and stearoamphoacetate.

In one embodiment, the amphoteric surfactant comprises sodium lauroampoacetate, sodium lauroampopropionate, disodium lauroampodiacetate, sodium cocoamphoacetate, disodium cocoamphodiacetate or a mixture thereof.

Suitable Zwitterionic surfactants are known compounds. Any Zwitterionic surfactant that is acceptable for use in the intended end use application and is chemically stable at the required formulation pH is suitable as the optional Zwitterionic surfactant component of the composition of the present invention, including, for example, those which can be broadly described as derivatives of aliphatic quaternary ammonium, phosphonium, and sulfonium compounds in which the aliphatic radicals can be straight chain or branched and wherein one of the aliphatic substituents contains from about 8 to about 24 carbon atoms and one contains an anionic water-solubilizing group such as carboxyl, sulfonate, sulfate, phosphate or phosphonate. Specific examples of suitable Zwitterionic surfactants include alkyl betaines, such as cocodimethyl carboxymethyl betaine, lauryl dimethyl carboxymethyl betaine, lauryl dimethyl alpha-carboxy-ethyl betaine, cetyl dimethyl carboxymethyl betaine, lauryl bis-(2-hydroxy-ethyl)carboxy methyl betaine, stearyl bis-(2-hydroxy-propyl)carboxymethyl betaine, oleyl dimethyl gamma-carboxypropyl betaine, and lauryl bis-(2-hydroxypropyl)alpha-carboxyethyl betaine, amidopropyl betaines, and alkyl sultaines, such as cocodimethyl sulfopropyl betaine, stearyldimethyl sulfopropyl betaine, lauryl dimethyl sulfoethyl betaine, lauryl bis-(2-hydroxy-ethyl)sulfopropyl betaine and alkylamidopropylhydroxy sultaines.

In one embodiment, the personal care composition further comprises an electrolyte, typically in an amount of up to about 20 pbw per 100 pbw of the personal care composition. Suitable electrolytes are known compounds and include salts of multivalent anions, such as potassium pyrophosphate, potassium tripolyphosphate, and sodium or potassium citrate, salts of multivalent cations, including alkaline earth metal salts such as calcium chloride and calcium bromide, as well as zinc halides, barium chloride and calcium nitrate, salts of monovalent cations with monovalent anions, including alkali metal or ammonium halides, such as potassium chloride, sodium chloride, potassium iodide, sodium bromide, and ammonium bromide, alkali metal or ammonium nitrates, and polyelectrolytes, such as uncapped polyacrylates, polymaleates, or polycarboxylates, lignin sulfonates or naphthalene sulfonate formaldehyde copolymers.

In one embodiment, the personal care composition comprises water, an anionic surfactant, a structuring agent for the anionic surfactant, and a pH responsive polymer according to the present invention and exhibits one or more lamellar surfactant phases. "Lamellar surfactant phases" are phases which comprise one or more surfactant bilayers, typically a plurality of surfactant bilayers separated by liquid medium. Lamellar phases include spherulite phases and the typical form of the liquid crystal G-phase, as well as mixtures thereof. "G-phases", which are sometimes referred to in the literature as "$L_\alpha$ phases", are typically pourable, non-Newtonian, anisotropic products that are cloudy looking and exhibit a characteristic "smeary" appearance on flowing. Lamellar phases can exist in several different forms, including domains of parallel sheets, which constitute the bulk of the typical G-phases described above and spherulites formed from a number of concentric spherical shells, each of which is a bilayer of surfactant. In this specification the term "G-phase" will be reserved for compositions, which are at least partly of the former type. The spherulites are typically between 0.1 and 50 microns in diameter and so differ fundamentally from micelles. The surfactant phase morphology of the structured surfactant composition is observed, for example, using an optical microscope under cross-polarized light at about 40× magnification.

In one embodiment, the personal care composition of the present invention exhibits structured surfactant properties, that is, shear-thinning viscosity and a capacity to suspend water insoluble or partially water soluble components.

As used herein in reference to viscosity, the terminology "shear-thinning" means that such viscosity decreases with an increase in shear rate. Shear-thinning may be characterized as a "non-Newtonian" behavior, in that it differs from that of a classical Newtonian fluid, for example, water, in which viscosity is not dependent on shear rate.

As used herein in reference to a component of an aqueous composition, the terminology "water insoluble or partially water soluble components" means that the component is present in the aqueous composition at a concentration above the solubility limit of the component so that, in the case of a water insoluble component, the component remains substantially non-dissolved in the aqueous composition and, in the case of a partially water soluble component, at least a portion of such component remains undissolved in the aqueous composition.

As used herein, characterization of an aqueous composition as "capable of suspending", or as being "able of suspend" water insoluble or partially water insoluble components means that the composition substantially resists flotation of such components in the composition or sinking of such components in such composition so that such components appear to be neutrally buoyant in such composition and remain at least substantially suspended in such composition under the anticipated processing, storage, and use conditions for such aqueous composition.

In one embodiment, the personal care composition of the present invention comprises, based on 100 pbw of the composition from about 5 to about 40 parts pbw, more typically from about 10 to about 30 pbw, and still more typically from about 15 to about 25 pbw, of the anionic surfactant and from about 0.1 to about 25 pbw, more typically, from about 0.5 to about 10 pbw, of a structuring agent.

In one embodiment, the pH of the lamellar phase containing personal care composition is from about 5.0 to about 7.0, more typically from about 5.5 to about 6.5.

Suitable anionic surfactants include those described above. In one embodiment of the lamellar phase containing personal care composition, the anionic surfactant comprises one or more branched and/or unsaturated anionic surfactants. Suitable branched anionic surfactants include, for example, sodium trideceth sulfate, sodium tridecyl sulfate, ammonium trideceth sulfate, and ammonium tridecyl sulfate.

Suitable structuring agents include cationic surfactants, amphoteric surfactants, fatty alcohols, alkoxylated alcohols, fatty acids, fatty acid esters, alkanolamides, amine oxides, and electrolytes, and mixtures thereof. An effective amount of such structuring agent is one that promotes and/or does not interfere with the formation of a lamellar surfactant phase. Suitable cationic surfactants, amphoteric surfactants, fatty alcohols, alkoxylated alcohols, fatty acids, fatty acid esters, alkanolamides, amine oxides, and electrolytes are described above.

Typically, the greater the amount of surfactant present in relation to its solubility, the smaller the amount electrolyte that may be required in order to form a structure capable of supporting solid materials and/or to cause flocculation of the structured surfactant. In one embodiment, the composition contains a sufficient amount of an electrolyte to promote formation lamellar surfactant phases.

In one embodiment, the personal care composition of the present invention further comprises, typically in an amount of from greater than 0 pbw to about 50 pbw, more typically form about 1 to about 30 pbw, per 100 pbw of the personal care composition, one or more "benefit agents" that is, materials that provide a personal care benefit, such as moisturizing or conditioning, to the user of the personal care composition, such as, for example, emollients, moisturizers, conditioners, polymers, vitamins, abrasives, UV absorbers, antimicrobial agents, anti-dandruff agents, fragrances, and/or appearance modifying additives, such as, for example, colored particles or reflective particles, which may be in the form of a solid, liquid, or gas and may be insoluble or are only partly soluble in the personal care composition. Mixtures of the benefit agents may be used.

In one embodiment, the personal care composition is a hair styling composition. Suitable hair styling compositions may be in the form of a gel, mousse, or spray and may be applied to the hair and/or skin, for example, by hand or by spraying, as appropriate in view of the form of the composition.

In one embodiment, the personal care composition is a hair styling gel that comprises a hair styling polymer, a pH responsive polymer of the present invention, and a carrier, such as water, a (C2-C6)alkanol, or a mixture thereof.

Suitable hair styling polymers typically comprise multiple cationic sites per molecule and include, for example, polyquaternium-11, polyquaternium4, polyquaternium-7, polyquaternium-16, polyquaternium-28, polyquaternium-44, polyquaternium-46, polyquaternium-55, polyquaternium-68 and polyquaternium-88. Suitable hair styling polymers also include, but are not limited to copolymers of polyvinylpyrrolidone, vinyl acetate, polyvinylcaprolactam, methylether maleic acid, acrylamides, octylacrylamide, butylaminoethyl, crotonic acid, dimethylaminopropyl methacrylate and dimethylaminoethyl methacrylate, and mixtures thereof.

As used herein, the term "mousse" means a composition that is in the form of a foam when applied. In one embodiment, the personal care composition is a hair styling mousse is packaged in a pressurized container and comprises a hair styling polymer, a pH responsive polymer of the present invention, a carrier, such as water, a (C2-C6)alkanol, a propellant suitable for foaming the composition when the composition is dispensed from the container. Suitable propellants are liquefiable gases, such as, for example, propane, butane, isobutane, nitrogen, carbon dioxide, nitrous oxide, 1,2-difluoroethane.

In one embodiment, the personal care composition is a hair spray composition suitable for spray application from a container that is equipped with a mechanical sprayer, comprising a hair styling polymer, a pH responsive polymer of the present invention, and a carrier, such as water, a (C2-C6)alkanol, or a mixture thereof.

In one embodiment, the personal care composition is an aerosol hair spray composition suitable for spray application from a pressurized container and comprises, a hair styling polymer, a carrier, typically a (C1-C6)alkanol or a (C7-C10) isoparaffin, a pH responsive polymer of the present invention, and a propellant suitable for aerosol delivery of the hair spray composition to the hair. Suitable propellants are those described above in regard to the hair styling mousse embodiment of the personal care composition of the present invention.

The hair styling gel, mousse, and hair spray may in each case, optionally further comprise one or more emollients, conditioning agents, shine enhancers, moisture and heat sensitive moieties, or a mixture thereof. Suitable emollients include, for example, PEG-40 castor oil, glycerol, propylene glycol, butylene glycol. Suitable conditioning and shine agents include, for example, quaternized and/or hydrolyzed proteins of honey, soy, wheat, guar or maize, cetyl alcohol, stearyl alcohol, ceteareth-20, isopropyl palmitate, cyclopentasiloxane, cyclomethicone, trimethylsilyamodimethicone, phenyltrimethicone, ethoxylated/propylated dimethicone, dimethiconol, panthenol, tocopherol acetate, tocopherol, cetrimmonium chloride, hair keratin and silk amino acids and ethoxylated/propoxylated waxes of fruit and vegetable origin.

The personal care composition according to the present invention may optionally further comprise one or more adjuvants, such as, for example, preservatives such as benzyl alcohol, methyl paraben, propyl paraben and imidazolidinyl urea; pH adjusting agents such as citric acid, succinic acid, phosphoric acid, sodium hydroxide, sodium carbonate; dyes, and sequestering agents such as disodium ethylenediamine tetra-acetate.

In general, personal care compositions may optionally comprise, based on 100 pbw of the personal care composition and independently for each such adjuvant, from about 0 to about 10 pbw, typically from 0.5 pbw to about 5.0 pbw, of such optional adjuvants, depending on the desired properties of the personal care composition.

The compounds of the present application are also useful as a component in aqueous fluid compositions used in oilfield applications.

In one embodiment, an aqueous fluid composition of the present invention comprises water and a pH responsive polymer of the present invention, typically from about 0.05 to about 40 pbw, more typically 0.1 pbw to 20 pbw, even more typically form about 1 to about 10 pbw of the pH responsive polymer per 100 pbw composition, wherein the pH of the composition is greater than or equal to about 6, more typically, from about 6 to about 10.

IX. Use with Materials in Geological Formations Fracturing Fluids

In one embodiment, the aqueous fluid composition of the present invention is used as the fracturing fluid in a method for hydraulic fracturing of a geologic formation to stimulate the production of fluids, such as oil and/or natural gas, from the formation. The fracturing fluid is injected through a wellbore and against a surface of the formation at a pressure and flow rate at least sufficient to initiate and/or extend one or more fractures in the formation. Typically, the fracturing fluid further comprises a proppant dispersed in the fracturing fluid. Suitable proppants are inorganic particles, such as sand, bauxite particles, or glass beads and are typically in the range of from about 20 to about 40 mesh. Such fracturing fluid compositions typically contain, based on 100 pbw of the liquid component of such composition, from about 90 pbw to about 100 pbw water, from about 0.1 pbw to about 10 pbw pH responsive polymer, and from about 10 pbw to about 150 pbw proppant. The proppant particles are transported into fractures in the geologic formation by the pressurized fracturing fluid stream and keep the fractures from closing back down when the stream of fracturing fluid is discontinued. The proppant-filled fractures provide permeable channels through which the formation fluids can flow to the wellbore and then be withdrawn. Hydraulic fracturing fluids are subject to high temperatures and shear rates.

The polymer and composition of the present invention may be used in the fracturing fluid in an amount of from 0.01 to 5% by weight of the fluid.

Crosslinking Agent

A crosslinking agent may be used with the fracturing fluids. The crosslinking agents used may include aluminum or antimony or Group 4 transition metal compound crosslinking agents. The crosslinking agent may include zirconium, titanium and hafnium crosslinking agents, and combinations of these, and may include organo-metallic compounds. Examples of suitable zirconium crosslinking agents include zirconium triethanolamine, L-glutamic acid-triethanolamine-zirconium, zirconium diethanolamine, zirconium tripropanolamine, and zirconium lactate complexes, and/or the related salts, and/or their mixtures. Examples of titanium crosslinking agents include titanium triethanolamine, dihydroxybis(ammonium lactato)titanium, and titanium acetylacetonate. The crosslinking agent may be included in the fluid in an amount of from about 0.01% to about 1.5% by weight of the fluid, more particularly, from about 0.02% to about 0.3% by weight of the fluid.

Buffering Agent

A hydroxyl ion releasing agent or buffering agent may be employed to adjust the pH or buffer the fluid, i.e., moderate amounts of either a strong base or acid may be added without causing any large change in pH value of the fluid. These may useful in changing the rate of crosslinking. Alkaline amine or polyamine compounds useful to raise the pH to the desirable level are outlined in U.S. Pat. No. 4,579,670, and include tetramethylenediamine, triethylenetetramine, tetraethylenepentamine (TEPA), diethylenetriamine, triethylenediamine, triethylenepentamine, ethylenediamen and similar compounds. The alkali metal hydroxides, e.g., sodium hydroxide, and carbonates can also be used. Other acceptable materials are $Ca(OH)_2$, $Mg(OH)_2$, $Bi(OH)_3$, $Co(OH)_2$, $Pb(OH)_2$, $Ni(OH)_2$, $Ba(OH)_2$, and $Sr(OH)_2$. Acids such as hydrochloric acid, sulfuric acid, nitric acid, citric acid, acetic acid, fumaric acid, maleic acid, can be used to lower the pH.

In various embodiments, the buffering agent is a combination of a weak acid and a salt of the weak acid; an acid salt with a normal salt; or two acid salts. Examples of suitable buffering agents are acetic acid-Na acetate; $NaH_2PO_4$—$Na_2PO_4$; sodium carbonate-sodium bicarbonate; and sodium bicarbonate, or other like agents. By employing a buffering agent instead of merely a hydroxyl ion producing material, a fluid is provided which is more stable to a wide range of pH values found in local water supplies and to the influence of acidic materials located in formations and the like.

Gas Component

The fracturing fluids may contain a gas component, as discussed above. The gas component may be provided from any suitable gas that forms an energized fluid or foam when introduced into the aqueous medium. See, for example, U.S. Pat. No. 3,937,283 (Blauer et al.), hereinafter incorporated by reference. The gas component may comprise a gas selected from nitrogen, air, argon, carbon dioxide, and any mixtures thereof. Particularly useful are the gas components of nitrogen or carbon dioxide, in any quality readily available. The gas component may assist in the fracturing, and also the capacity of the fluid to carry solids, such as proppants. The presence of the gas also enhances the flowback of the fluid to facilitate cleanup. The fluid may contain from about 10% to about 90% volume gas component based upon total fluid volume percent, more particularly from about 20% to about 80% volume gas component based upon total fluid volume percent, and more particularly from about 30% to about 70% volume gas component based upon total fluid volume percent.

Breaker

Fracturing fluids based on the invention may also comprise a breaker. The purpose of this component is to "break" or diminish the viscosity of the fluid so that this fluid is more easily recovered from the formation during cleanup. With regard to breaking down viscosity, oxidizers, enzymes, or acids may be used. Breakers reduce the polymer's molecular weight by the action of an acid, an oxidizer, an enzyme, or some combination of these on the polymer itself. The breakers may include persulfates such as ammonium persulfate, sodium persulfate, and potassium persulfate, bromates such as sodium bromate and potassium bromate, periodates, metal peroxides such as calcium peroxide, chlorites, and the like, and the combinations of these breakers, live or encapsulated.

Proppant

Embodiments of the invention used as fracturing fluids may also include proppant particles substantially insoluble in the fluids of the formation. Proppant particles carried by the treatment fluid remain in the fracture created, thus propping open the fracture when the fracturing pressure is released and the well is put into production. Suitable proppant materials include, but are not limited to, sand, walnut shells, sintered bauxite, glass beads, ceramic materials, naturally occurring materials, or similar materials. Mixtures of proppants can be used as well. If sand is used, it will typically be from about 20 mesh (0.841 mm) to about 100 mesh (0.0059 mm) in size. With synthetic proppants, mesh sizes of about 8 (0.937 mm) or greater may be used. Naturally occurring materials may be underived and/or unprocessed naturally occurring materials, as well as materials based on naturally occurring materials that have been processed and/or derived. Suitable examples of naturally occurring particulate materials for use as proppants include, but are not necessarily limited to: ground or crushed shells of nuts such as walnut, coconut, pecan, almond, ivory nut, brazil nut, etc.; ground or crushed seed shells (including fruit pits) of seeds of fruits such as plum, olive, peach, cherry, apricot, etc.; ground or crushed seed shells of other plants such as maize (e.g., corn cobs or corn kernels), etc.; processed wood materials such as those derived from woods such as oak, hickory, walnut, poplar, mahogany, etc. including such woods that have been processed by grinding, chipping, or other form of particalization, processing, etc. Further information on nuts and composition thereof may be found in Encyclopedia of Chemical Technology, Edited by Raymond E. Kirk and Donald F. Othmer, Third Edition, John Wiley & Sons, Volume 16, pages 248-273 (entitled "Nuts"), Copyright 1981, which is incorporated herein by reference.

The concentration of proppant in the fluid can be any concentration known in the art, and will preferably be in the range of from about 0.03 to about 3 kilograms of proppant added per liter of liquid phase. Also, any of the proppant particles can further be coated with a resin to potentially improve the strength, clustering ability, and flow back properties of the proppant.

Aqueous Media

The aqueous medium of the fracturing fluids of the present invention may be water or brine. In those embodiments of the invention where the aqueous medium is a brine, the brine is water comprising an inorganic salt or organic salt. Inorganic salts may include alkali metal halides, such as potassium chloride. The carrier brine phase may also comprise an organic salt, such as sodium or potassium formate. Inorganic divalent salts include calcium halides, such as calcium chloride or calcium bromide. Sodium bromide, potassium bromide, or cesium bromide may also be used. The salt may be chosen for compatibility reasons i.e. where the reservoir drilling fluid used a particular brine phase and the completion/clean up fluid brine phase is chosen to have the same brine phase. Typical salt levels are 2 to 30 wt % salt based on overall composition of the aqueous brine. The most common level of salt in brine is 2-10 weight % sodium chloride, potassium chloride or mixtures thereof based on overall composition of the aqueous brine.

Fiber Component

A fiber component may be included in the fracturing fluids of the invention to achieve a variety of properties including improving particle suspension, and particle transport capabilities, and gas phase stability. Fibers used may be hydrophilic or hydrophobic in nature, but hydrophilic fibers may be useful for some applications. Fibers can be any fibrous material, such as, but not necessarily limited to, natural organic fibers, comminuted plant materials, synthetic polymer fibers (by non-limiting example polyester, polyaramide, polyamide, novoloid or a novoloid-type polymer), fibrillated synthetic organic fibers, ceramic fibers, inorganic fibers, metal fibers, metal filaments, carbon fibers, glass fibers, ceramic fibers, natural polymer fibers, and any mixtures thereof. Particularly useful fibers are polyester fibers coated to be highly hydrophilic, such as, but not limited to, DACRON polyethylene terephthalate (PET) fibers available from Invista Corp. Wichita, Kans., USA, 67220. Other examples of useful fibers include, but are not limited to, polylactic acid polyester fibers, polyglycolic acid polyester fibers, polyvinyl alcohol fibers, and the like. When used in fluids of the invention, the fiber component may be include at concentrations from about 1 to about 15 grams per liter of the liquid phase of the fluid, in certain applications the concentration of fibers may be from about 2 to about 12 grams per liter of liquid, and in others from about 2 to about 10 grams per liter of liquid.

Other Optional Ingredients

Fluid embodiments of fracturing fluids of the invention may further contain other additives and chemicals known to be commonly used in oilfield applications by those skilled in the art. These include, but are not necessarily limited to, materials such as surfactants in addition to those mentioned herein, clay stabilizers such as tetramethyl ammonium chloride and/or potassium chloride, breaker aids in addition to those mentioned herein, oxygen scavengers, alcohols, scale inhibitors, corrosion inhibitors, fluid-loss additives, bactericides, and the like. Also, they may include a co-surfactant to optimize viscosity or to minimize the formation of stable emulsions that contain components of crude oil or a polysaccharide or chemically modified polysaccharide, polymers such as cellulose, derivatized cellulose, guar gum, derivatized guar gum, xanthan gum, or synthetic polymers such as polyacrylamides and polyacrylamide copolymers, oxidizers such as ammonium persulfate and sodium bromate, and biocides such as 2,2-dibromo-3-nitrilopropionamine. The fluid should be substantially devoid of hectorite clay or other clay components and such components may be present in the fluid only in amounts of less than 0.1% by weight.

Aqueous fluid embodiments of the invention may also comprise an organoamino compound. Examples of suitable organoamino compounds include, but are not necessarily limited to, tetraethylenepentamine (TEPA), triethylenetetramine, pentaethylenehexamine, triethanolamine, and the like, or any mixtures thereof. When organoamino compounds are used in fluids of the invention, they are incorporated at an amount from about 0.01 wt % to about 2.0 wt % based on total liquid phase weight. The organoamino compound may be incorporated in an amount from about 0.05 wt % to about 1.0 wt % based on total weight of the fluid. A particularly useful organoamino compound is tetraethylenepentamine (TEPA).

Hydraulic Fracturing Techniques

The fluids of the invention may be used for hydraulically fracturing a subterranean formation. Techniques for hydraulically fracturing a subterranean formation are known to persons of ordinary skill in the art, and involve pumping the fracturing fluid into the borehole and out into the surrounding formation. The fluid pressure is above the minimum in situ rock stress, thus creating or extending fractures in the formation. See Stimulation Engineering Handbook, John W. Ely, Pennwell Publishing Co., Tulsa, Okla. (1994), U.S. Pat. No. 5,551,516 (Normal et al.), "Oilfield Applications", Encyclopedia of Polymer Science and Engineering, vol. 10, pp. 328-366 (John Wiley & Sons, Inc. New York, N.Y., 1987) and references cited therein, the disclosures of which are incorporated herein by reference thereto.

In the fracturing treatment, fluids of the present invention may be used in the pad treatment, the proppant stages, or both. The components of the liquid phase may be mixed on the surface. Alternatively, the fluid may be prepared on the surface and pumped down tubing while any gas component could be pumped down the annulus to mix down hole, or vice versa.

In hydraulic fracturing the fracturing fluid comprising water soluble polymer and at least one nonionic surfactant is pumped into the targeted formation at a rate in excess of what can be dissipated through the natural permeability of the formation rock. The fracturing fluids result in a pressure build up until such pressure exceeds the strength of the formation rock. When this occurs, the formation rock fails and a so-called "fracture" is initiated. With continued pumping, the fracture grows in length, width and height.

At a predetermined time in the pumping process, solid particulate is typically added to the fluid that is being pumped. This particulate is carried down the well, out of the wellbore and deposited in the created fracture. It is the purpose of this specially designed particulate to keep the fracture from "healing" to its initial position (after pumping has ceased). The particulate is said to be propping open the fracture and is therefore designated as "proppant". The fracture, which is generated by the application of this stimulation technique, creates a conductive path to the wellbore for the hydrocarbon.

Typical proppant is selected from the group consisting of gravel, quartz sand grains, sintered bauxite, glass and ceramic beads, walnut shell fragments, or aluminum pellets. The fracturing fluid may also include a thermal stabilizer, for example sodium thiosulfate, methanol, ethylene glycol, isopropanol, thiourea, and/or sodium thiosulfite. The fracturing fluid may also include KCl as a clay stabilizer.

X. Home Care or Industrial Care Compositions

In one embodiment, the present invention is directed to a home care or industrial cleaning composition, such as a liquid detergent, a laundry detergent, a hard surface cleanser, a dish wash liquid, or a toilet bowl cleaner, comprising water, one or more surfactants, and a polymer of the present invention. Suitable surfactants include those described above in regard to the personal care composition embodiments of the present invention. Such cleaning compositions may optionally further comprise one or more of water miscible organic solvents, such as alcohols and glycols, and/or one or more additives.

Suitable additives are known in the art and include, for example, organic builders, such as organophosphonates, inorganic builders, such as ammonium polyphosphates, alkali metal pyrophosphates, zeolites, silicates, alkali metal borates, and alkali metal carbonates, bleaching agents, such as perborates, percarbonates, and hypochlorates, sequestering agents and anti-scale agents, such as citric acid and ethylenediaminetetraacetic acid, inorganic acids, such as phosphoric acid and hydrochloric acid, organic acids, such as acetic acid, abrasives, such as silica or calcium carbonate, antibacterial agents or disinfectants, such as triclosan and cationic biocides, for example (N-alkyl)benzyldimethylammonium chlorides, fungicides, enzymes, opacifing agents, pH modifiers, dyes, fragrances, and preservatives.

In an embodiment the home care or industrial cleaner benefit agent is selected from the group consisting of soil release agents, fabric softener, surfactants, builders, binders, bleach and fragrances.

In an embodiment the home care or industrial cleaning composition for cleaning fabrics or hard surfaces comprising, the composition of the present invention and a surfactant and a home care or industrial cleaner benefit agent.

In an embodiment the composition is a detergent composition and comprises: the polymer, at least one detersive surfactant, and a builder.

The invention also encompasses a method for cleaning a substrate selected from the group consisting of a hard surface and a fabric, comprising applying the composition of the present invention to the substrate.

Experiments

1. Tri-substituted phenol ethoxylates surfactants as emulsifiers in emulsion polymerization:

The tri-substituted phenol ethoxylates were synthesized by reacting ethylene oxide with the corresponding tri-substituted phenol hydrophobe at greater than 130 degC (typically greater than 140 degC) using less than 0.5 (based on base charge) potassium hydroxide to catalyze the reaction. A maximum reactor pressure of about 5 bar was maintained throughout the two hours ethylene oxide feed. Reaction was neutralized with acetic acid and product was characterized. The three tri-substituted phenol ethoxylates used in this study were synthesized and the ethylene oxide amount was calculated by 13C NMR and results are shown on Table 1 (wherein "EO" is shorthand for "Ethylene Oxide" wherein, for example, 10EO means "about" 10 ethylene oxide units).

TABLE 1

Tri-substituted Phenol Ethoxlates

| Sample ID | Chemical Description | Mol. TSP/DSP | Mol Ethylene Oxide (EO) |
|---|---|---|---|
| R1146-022 | 4tBDSP + 10EO | 97/3.3 | 10.3 |
| R1146-026 | NDSP + 10EO | 97/3.1 | 10.1 |
| R1146-028 | MDSP + 10EO | 98/1.8 | 10.7 |

The general chemical structure of the above products synthesized is as follow (exemplary):

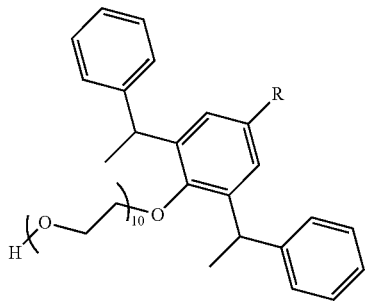

R=t-butyl (4tB), nonyl (N), dodecyl (D) and methyl (M)

2. Tri-substituted phenol ethoxylates.

Tri-substituted phenol ethoxylate—sulfate surfactants

The ethoxylated products were converted to anionic surfactants by reacting them with sulfamic acid. The amount of anionic surfactant produced was determined by titration using hyamine and results are shown below.

The following procedure is a representative one and it is as follows:

Melt ethoxylate in the oven as needed and ensure a low percent of moisture. Into the reactor 160.42 grams of melted nonyl distyrylphenol-10 EO were added. The ethoxylate was allowed to equilibrate under continuous stirring and in presence of nitrogen. After a period of one hour purging with nitrogen to remove dissolved oxygen in the ethoxylate, sulfamic acid is added. Sulfamic acid is added in five equal shots over one hour. The oxygen purging step is important to minimize color formation.

At the conclusion of sulfamic acid feed, the reactor temperature was raised to 90° C. and held for five hours. After cooling, determine percent of actives, acid number, free sulfamic acid and pH.

TABLE 2

Anion actives characterization of tert-butyldistyrylphenol - 10 EO - sulfate, nonyldistyrylphenol - 10 EO - sulfate and methyldistyrylphenol - 10 EO - sulfate surfactants.

| Sample ID | Chemical Description | Actives (%) Hyamine 1622 | % Mol EO (Exp.) |
|---|---|---|---|
| S1169-009 | 4tBDSP + 10EO | 69.5 | 10.3 |
| S1169-011 | NDSP + 10EO | 97.4 | 10.1 |
| S1169-054 | MDSP + 10EO | 87.7 | 10.7 |

Background on Monomer Emulsion Stability:

Emulsions are defined as colloidal systems in which fine droplets of one liquid are dispersed in another liquid, where the two liquids are mutually immiscible. Two immiscible liquids cannot form a stable emulsion. Therefore, a surfactant is usually added to facilitate creation and stabilization of the emulsion. Surfactant type, surfactant concentration, monomer to water ratio, addition order, mixing time, and the type and speed of stirrer can influence the ability to obtain a good monomer emulsion. The stability of the monomer emulsion can affect the quality of the ensuing emulsion polymerization.

The three tri-substituted phenol ethoxylate—sulfates (1169-009, 1169-011 and S1169-054-01) tested produced visually stable monomer emulsions (1.5% BOTM)

Polymerization Procedure:

To test the capability to form a stable pre-emulsion, monomer emulsions were prepared using a calculated amount of methyl acrylic acid, butyl acrylate and methyl methacrylate with the associated surfactant and deionized water. Mixing was conducted with a mechanical stirrer until a stable monomer emulsion was formed (no phase separation observed) if possible.

The full acrylic copolymerization of methacrylic acid, butyl acrylate, and methyl methacrylate with ammonium persulfate as initiator was carried out using a reactor system under slight $N_2$ pressure. The vinyl acrylic copolymerization of acrylic acid, butyl acrylate, and vinyl acetate with ammonium persulfate as initiator was carried out using a reactor system under slight $N_2$ pressure. The reactor system includes a mechanical stirrer, condenser, thermocouple, monomer and initiator feed lines. A typical emulsion polymerization is as follows: into the reactor deionized water and monomer (e.g., NDSP+10 EO) are added. The mixture is allowed to equilibrate and then the monomer emulsion seed were added. After a seeding period, the remaining monomer emulsion and initiator solution are fed. At the conclusion of feeds, the reactor temperature was cooled to room temperature. The tri-substituted phenol ethoxylate—sulfate surfactants were evaluated in the acrylic systems described above at surfactant loading level of 1.5% BOTM.

Emulsion polymerization in the presence of methyldistyrylphenol-10EO—sulfate (MDSP-10EO), 4tert-butyldistyrylphenol-10EO-sulfate (4tBDSP-10EO); and nonyldistyrylphenol-10EO—sulfate (NDSP-10EO), are described herein. Performance of MDSP-10EO—sulfate (1169-054), 4tBDSP-10EO—sulfate (1169-009) and NDSP-10EO—sulfate (1169-011) were evaluated by using the same standard polymerization procedure. MDSP-10EO—sulfate (1169-054), 4tBDSP-10EO—sulfate (1169-009) and NDSP-10EO—sulfate (1169-011) concentrations were adjusted to achieve identical actives level in the recipe (1.5% BOTM). Particle size results are favorably and close to 100 nm (Table 3).

TABLE 3

Polymerization conditions and latex characterization for tri-substituted phenol ethoxylate-sulfate surfactants

| Polymerization | Surfactant | BOTM (%) | Solids (%) | Coagulum (%) | Particle Size (nm) | PDI | ME Stability |
|---|---|---|---|---|---|---|---|
| S1177-09-01 | NDSP-10EO | 1.5 | 41.9 | 0.12 | 103.9 | 0.02 | Stable |
| S1177-11-01 | 4tBDSP-10EO | 1.5 | 41.2 | 0.10 | 96.5 | 0.04 | Stable |
| S1177-88-01 | MDSP-10EO | 1.5 | 43.8 | 0.31 | 108.1 | 0.07 | Not Stable |

In all cases monomer emulsions were visually stable during the polymerization. The emulsion polymerization experiments suggest that the tri-substituted phenol ethoxylate—sulfates, 4tert-butyldistyrylphenol-10EO-sulfate (4tBDSP-10EO); and nonyldistyrylphenol-10EO—sulfate (NDSP-10EO), could be used as surfactants, while methyldistyrylphenol-10EO—sulfate (MDSP-10EO) is not suitable under similar conditions.

2. Tri-Substituted Phenol Ethoxylate Surfactants as Additives in Latex (Emulsions) to Improve Freeze Thaw Background on latex freeze thaw improvement. Benefits of trisubstituted phenol surfactants in latex freeze thaw improvement were examined and Soprophor TS10 and Soprophor BSU were used as control. The surfactants chemical structure is shown below (10 and 16 units of EO).

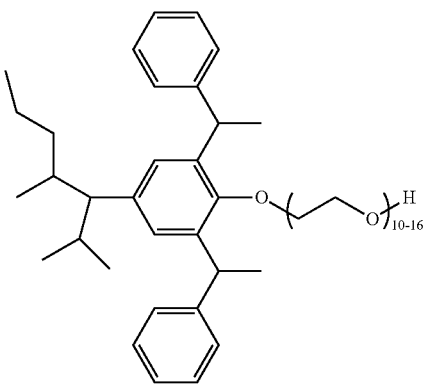

nonyldistyrylphenol-10-16EO

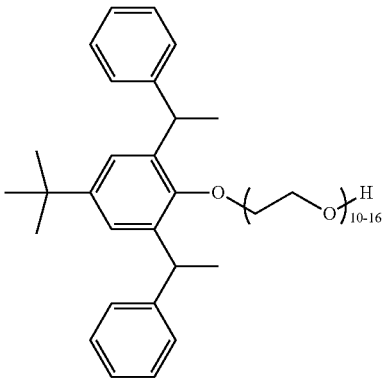

4tert-butyldistyrylphenol-10-16EO

Acronal optive 130 was used as binder (resin-latex) to assess the benefits. Trisubstituted phenol ethoxylate surfactants were added to Acronal Optive 130 under continuous agitation according to the procedure below:

EQUIPMENT: ½ pint aluminum can with lid, Stirrer, Timer.

PROCEDURE: 170 grams of Optive 130 is weighed and placed in beaker. The Optive 130 is then stirred. The additive is then added drop wise as the Optive 130 is stirring. The mixture is allowed to run for 20 minutes after the addition is complete. The mixture is then let to sit overnight closed to settle. The BV is taken after the mixtures sits overnight. After sitting overnight samples were placed in a freezer according to the following procedure:

EQUIPMENT: ½ pint aluminum can with lid, Freezer

PROCEDURE: 170 of grams of latex is weighed and placed in aluminum container with the lid fastened. The container is placed in secondary containment in the center of a −15° C. freezer for 17 hours. If more than one container is placed in the freezer, there needs to be at least 1 inch between cans. The sample is removed from the freezer and let to return to room temperature for 7 hours. The sample is then observed visually to see if it passed the cycle. Dependent on if the sample passes, the cycle maybe repeated up to 5 times. After completion of the specified number of cycles, compare the test sample with the latex store at room temperature. Examine the test sample for any evidence of settling, gelation or coagulation To test the capability to improve latex freeze thaw, Brookfield viscosity was measured for all samples after each cycle. The tri-substituted phenol ethoxylates tested improved latex freeze thaw and latex samples passed 5 cycles.

3. Tri-substituted phenol ethoxylate surfactants as additives in paints: dispersants, freeze thaw and open time extender.

Efficiency and Optimum Usage Level Determination of Dispersant

Efficiency and optimum usage level of dispersant was determined by dispersant demand curve studies. Starting point formulation for demand curve varies depending on pigment. Typically, organic pigments can be evaluated at 40-50% pigment loading, while carbon blacks can vary from 10-50% pigment loading depending on their properties such as particle size and surface treatment.

Prepare a starting point formulation consisting of pigment, dispersant, defoamer, DI water, and base (if needed). Add the liquid ingredients including a small amount of dispersant to the grind pot and begin mixing at a low speed using a high shear (Cowles) disperser. After a homogeneous mixture has been obtained, slowly add the pigment. Once all of the pigment has been added, begin mixing at a maximum speed needed to create a strong vortex. After premix has finished, attach cooling water, add milling beads and prepare for milling. After 30 minutes milling, wait one minute and measure the viscosity via Brookfield viscometer. Continue add dispersant incrementally and mill for 4-6 minutes after each addition, and take the measurement for viscosity. Complete the test when the viscosity shows significant increase.

Freeze Thaw Stability Testing

The freeze-thaw stability of the paints was measured by ASTM standard test method D 2243. The procedure for this ASTM method is as follows: the samples were placed in the freezer overnight at 0° F. (−18° C.) for 17 hours. The samples were then removed from the freezer the next day and were allowed to "thaw out" at room temperature for 7 hours. The samples were then well mixed by hand using a spatula before measuring the viscosity.

Open Time Evaluation

Open time was evaluated according to a known, industry-wide used method that is currently being validated by ASTM. A black vinyl leneta scrub panel that was secured on an Aluminium Drawdown Plate in a constant humidity/temperature room (CTCH) was used as the substrate. The leneta scrub panel was divided into 8 horizontal sections. A 250 μm wet film thickness paint was drawn down using a Dow film caster. On each section, a mark (X) was made immediately after casting the paint, using the handle tip of the brush. Test paint was then applied in perpendicular sections, brushing each section across the initial casted section—in one direction. The perpendicular sections were repeated at 2 minutes time intervals—using the same number of brush strokes for each time interval. The coating was allowed to dry in the CTCH room for 24 hours prior to rating the results.

APPLICATION EXAMPLE

Example 1

The synthesized chemicals were evaluated as freeze-thaw stabilizer and open time extenders in architectural paint. A semi-gloss paint was formulated according to the formula listed below. Then the samples were post added to the paint at 1% active based on the total weight of paint. Freeze-thaw and open time properties were evaluated according to the procedure previously described.

TABLE 4 semi-gloss paint formula

| Raw materials | Pounds | Weight, % |
|---|---|---|
| Grind | | |
| Water | 80 | 7.78 |
| Rhodoline 286N | 8 | 0.78 |
| Rhodoline 643 | 0.5 | 0.05 |
| Antarox BL-225 | 0 | 0.00 |
| AMP-95 | 2 | 0.19 |
| Attagel 50 | 5 | 0.49 |
| Titanium dioxide Tiona 595 | 230 | 22.38 |
| Let down | | 0.00 |
| Water | 89.5 | 8.71 |
| Acronal Optive 130 | 480 | 46.70 |
| Rhodoline 643 | 2 | 0.19 |
| Aquaflow NHS310 | 23 | 2.24 |
| Water | 95 | 9.24 |
| Acrysol TT-935 | 8.8 | 0.86 |
| Polyphase 678 | 4 | 0.39 |
| Total | 1027.8 | 100.00 |

The experiments illustrate tri-substituted phenol ethylates improved the freeze-thaw stability of the paint. Most of them passed 5 cycles without significant viscosity increase, while the blank and control failed just after one cycle test.

TABLE 5 freeze-thaw stability test

| Acrylic semi gloss paint | 4tBDSP-10EO | 4tBDSP-16EO | NDSP-10EO | 4tBDSP-10EO sulfate | NDSP-10EO sulfate | Blend, NDSP-10EO/NDSP-10EO sulfate 50/50 | NP-9, control | Blank |
|---|---|---|---|---|---|---|---|---|
| 1st cycle, KU | 100.9 | 100.9 | 140.1 | 110.2 | 94.9 | 122.4 | Fail | Fail |
| 2nd cycle, KU | 109.2 | 101.4 | 128.4 | 111.2 | 128.8 | 111.4 | | |
| 3rd cycle, KU | 103.1 | 100.6 | 137.2 | 107.4 | 120.0 | 122.3 | | |
| 4th cycle, KU | 110.2 | 110.8 | Fail | 117.4 | 127.1 | 126.2 | | |
| 5th cycle, KU | 109.8 | 110.2 | | 126.4 | 136.4 | 136.6 | | |

The results also showed that the currently invented products significantly improved the open time of the paint.

TABLE 6

Open time test

| | Acrylic semi gloss paint | | |
|---|---|---|---|
| | MeDSP-10EO | MeDSP-16EO | MeDSP-25EO |
| Open time, min | 12 | 12 | 8 |
| | Acrylic semi gloss paint | | |
| | 4tBDSP-10EO | 4tBDSP-16EO | 4tBDSP-25EO |
| Open time, min | 10 | 12 | 8 |

TABLE 6-continued

Open time test

Acrylic semi gloss paint

| | NDSP-10EO | NDSP-16EO | NDSP-25EO |
|---|---|---|---|
| Open time, min | 10 | 12 | 10 |

Acrylic semi gloss paint

| | C12DSP-10EO | C12DSP-16EO | C12DSP-25EO |
|---|---|---|---|
| Open time, min | 10 | 12 | 12 |

Acrylic semi gloss paint

| | TSP-10EO | TSP-16EO | TSP-25EO |
|---|---|---|---|
| Open time, min | 10 | 12 | 12 |

Acrylic semi gloss paint

| | Blank | NP-9, control |
|---|---|---|
| Open time, min | 6 | 6 |

Dispersion Experiment: The pigment concentration was prepared according to the following procedure:

Add DI water, dispersant, defoamer, and ammonia to the grind pot and mix well. Then add pigment powder to the grind pot slowly under agitation at a low speed using a high shear (Cowles) disperser. Once all of the pigment has been added, begin mixing at high speed for 20 minutes. After premix has finished, attach cooling water, add milling beads and prepare for milling for 60 minutes or until the desired color strength and coloristic properties were obtained.

The new surfactants were evaluated as dispersants for carbon black, and the results are given in the table. The pigment concentration prepared by the currently invented dispersants showed very low initial viscosity and very stability on storage. It also showed excellent color strength development compared to the standard dispersion. The jetness and L value, as well as rub-up test were also comparable in comparison with the standard dispersion.

TABLE 7 carbon black concentration

| | Control | C1-DSP-16EO | C4-DSP-16EO | C9-DSP-16EO | C12-DSP-16EO |
|---|---|---|---|---|---|
| Pigment % (carbon black, Raven 1170) | 45% | 45% | 45% | 45% | 45% |
| Dispersant (dry/dry) | 18% | 18% | 18% | 18% | 18% |
| Initial, pH | 8.8 | 8.96 | 8.72 | 9.11 | 8.79 |
| Initial Viscosity, cps/60 rpm | 349.9 | 323.9 | 537.9 | 643.9 | 531.9 |
| 10 Day Heat Ageing at 50 C. viscosity stability | | | | | |
| Initial Viscosity, cps/60 rpm | 555.9 | 703.8 | 911.8 | 1168 | 1190 |
| Tinting results for gloss acrylic deepbase (12% w/w) | | | | | |
| KU deepbase "as is" | 102.2 | 102.2 | 102.2 | 102.2 | 102.2 |
| KU after dispersant | 98.6 | 84.8 | 87.1 | 101.5 | 104.6 |
| Gloss, 20° | 10.3 | 3.7 | 4.4 | 12 | 11.5 |
| Gloss, 60° | 47 | 32.8 | 35.4 | 49.4 | 47.6 |
| Masstone Color Strength | 100% | 103.60% | 104.48% | 102.25% | 101.60% |
| L* | 24.61 | 24.27 | 24.17 | 24.43 | 24.4 |
| B* | −0.2 | −0.27 | −0.17 | −0.19 | −0.21 |
| Tinting results for gloss acrylic white paint (2%, w/w) | | | | | |
| Tint Strength | 100% | 98.60% | 99.30% | 100.70% | 99.90% |
| Rub up ΔE | 1.02 | 0.8 | 0.98 | 0.82 | 1.2 |

The new surfactants were evaluated as dispersants for other organic pigment, and the examples for dispersion of phthalo blue 15:4 and organic yellow PY74 are given in the table. The pigment concentration prepared by the currently invented dispersants showed very low initial viscosity and very stability on storage. It also showed excellent color strength development compared to the standard dispersion.

TABLE 8

| | Control | C1-DSP-16EO | C4-DSP-16EO | C9-DSP-16EO |
|---|---|---|---|---|
| Pigment % (phthalo blue 15:4) | 45% | 45% | 45% | 45% |
| Dispersant (dry/dry) | 15% | 15% | 15% | 15% |
| Initial, pH | 9.1 | 9.1 | 9 | 8.7 |
| Initial Viscosity, cps/60 rpm | 236 | 160 | 274 | 586 |
| 10 Day Heat Ageing at 50 C. viscosity stability | | | | |
| Initial Viscosity, cps/60 rpm | 834 | 466 | 382 | 934 |

TABLE 8-continued

|  | Control | C1-DSP-16EO | C4-DSP-16EO | C9-DSP-16EO |
|---|---|---|---|---|
| Tinting results for gloss acrylic deepbase (12% w/w) | | | | |
| KU deepbase "as is" | 104.8 | 104.8 | 104.8 | 104.8 |
| KU after dispersant | 88.3 | 79.3 | 84.7 | 95.9 |
| Gloss, 20° | 19.5 | 19.5 | 18.4 | 19 |
| Gloss, 60° | 54 | 54 | 52.6 | 52.6 |
| Masstone Color Strength | 100% | 100.32% | 100.20% | 99.30% |
| Tinting results for gloss acrylic white paint (2%, w/w) | | | | |
| Tint Strength | 100% | 97.70% | 98.40% | 99.80% |
| Rub up ΔE | 1.39 | 1.4 | 1.12 | 1.01 |

TABLE 9

|  | Control | C1-DSP-16EO | C4-DSP-16EO | C9-DSP-16EO | C12-DSP-16EO |
|---|---|---|---|---|---|
| Pigment % (yellow PY74) | 50% | 50% | 50% | 50% | 50% |
| Dispersant (dry/dry) | 8% | 8% | 8% | 8% | 8% |
| Initial, pH | 9.4 | 9.3 | 9.4 | 9.5 | 9.6 |
| Initial Viscosity, cps/60 rpm | 190 | 380 | 375 | 210 | 150 |
| 10 Day Heat Ageing at 50 C. viscosity stability | | | | | |
| Initial Viscosity, cps/60 rpm | 336 | 542 | 486 | 326 | 270 |
| Tinting results for gloss acrylic deepbase (12% w/w) | | | | | |
| KU deepbase "as is" | 104.8 | 104.8 | 104.8 | 104.8 | 104.8 |
| KU after dispersant | 86.4 | 83 | 85.7 | 92.3 | 94.1 |
| Gloss, 20° | 14.2 | 14.2 | 13.6 | 14.7 | 14.2 |
| Gloss, 60° | 50.3 | 50.2 | 50.2 | 50.9 | 50.2 |
| Masstone Color Strength | 100% | 100.32% | 100.20% | 99.30% | 99.30% |
| Tinting results for gloss acrylic white paint (2%, w/w) | | | | | |
| Tint Strength | 100% | 100% | 100.70% | 104.80% | 103.90% |
| Rub up ΔE | 0.85 | 0.83 | 0.83 | 0.91 | 0.83 |

Experiment: Tri-substituted phenol surfactants as wetting agents.

This study assesses the benefits of trisubstituted phenol surfactants as wetting agents and, for comparison proposes, Soprophor BSU (Solvay) was used as control. The surfactants were evaluated using the Drave's wetting test which is described below.

Equipment: Special 40 gram weight with hook and string.
1000 ml graduated cylinder
2000 ml volumetric flask
1000 ml volumetric flask
250 ml beaker
250 ml graduated cylinder
Blender
Stop watch/timer
Unbleached Cotton
Procedure:

Using a 2000 ml volumetric flask for the 0.025 and 0.100 conc. (1000 ml vol. flask for the 0.050 conc.) add the amount of surfactant to flask, then partially fill flask with DI water.

Use a magnetic stir bar and mix until the surfactant is dissolved, then finish filling flask, this is The Solution.

Fill a 250 ml graduated cylinder with The Solution above the 250 ml line, and remove foam on the top, with a pipet.

Using the unbleached cotton, remove one ring and cut small knot. Form a figure 8 then fold like a rubber band, and attach special weight with hook and string, now cut other end. Remove small cotton strings by slapping against bench top and freeing the other strands. Time, drop weight and cotton into the 250 ml graduated cylinder and start timer. String between weight and hook starts to slacken stop timer, and record result. Run sample three times.

Referring to Table 10, Table 10 shows tri-substituted phenol ethoxylate—sulfate surfactants tested worked as wetting agents and the best performer is showed on the figure below (The lower the time(sec), generally the more effective the wetting agent, i.e., better wetting). Referring to Table 10, the 4tBDSP-16EO, at 0.025% and 0.1%, showed significantly better wetting than the comparative Soprophor BSU by a factor of about 10. Similar results were seen with 4tBDSP-16EO and 4tBDSP-16EO-sulfate as compared to the control (Sophrophor BSU).

TABLE 10

| Additive | Drave's wetting (time - seconds) | |
|---|---|---|
|  | 0.025% | 0.1% |
| Soprophor BSU | 900 | 187 |
| 4 tBDSP - 16 EO ethoxylate | 89 | 19 |
| 4 tBDSP - 10 EO ethoxylate | 197 | 40 |
| 4 tBDSP - 10 EO ethoxylate - sulfate | 50 | 22 |

It should be apparent embodiments other than those expressly described above come within the spirit and scope of the present invention. Thus, the present invention is not defined by the above description but by the claims appended hereto.

What is claimed is:

1. A surface active compound according to structure (D.I):

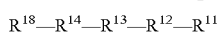

(D.I)

$R^{12}$ is absent or is a bivalent linking group, $R^{13}$ is bivalent polyether group, $R^{14}$ is absent or is a bivalent linking group;

$R^{18}$ is an anionic group, a cationic group or a nonionic group; and $R^{11}$ is a tri-substituted aromatic group according to the structure D.XII

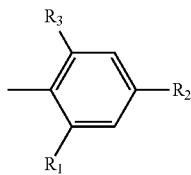
D.XII wherein $R_1$, $R_2$ and $R_3$ are independently selected from the following structures D.XIIIa, D.XIIIb, D.XIIIc, D.XIIId:

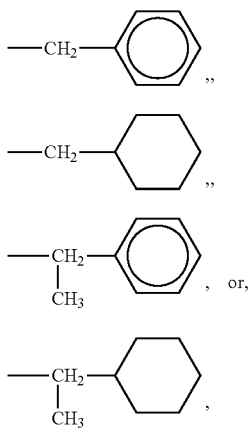

D.XIIIa

D.XIIIb

D.XIIIc

D.XIIId or a $C_4$-$C_{30}$ branched or linear alkyl group or alkenyl group;

wherein at least one of $R_1$, $R_2$ and $R_3$ is the $C_4$-$C_{30}$ branched or linear alkyl group or alkenyl group, and at least one of $R_1$, $R_2$ and $R_3$ is selected from structure D.XIIIa, D.XIIIb, D.XIIIc, or D.XIIId.

2. The compound of claim 1 wherein $R^{18}$ is —OH, —OCH$_3$, —OC$_2$H$_5$, —OC$_3$H$_7$, —OC$_4$H$_9$, —OC$_5$H$_{11}$, —OC$_6$H$_{13}$, —Cl, —Br, —CN, Phosphonate (—PO$_3^-$M$^+$), Phosphate (PO$_4^-$M$^+$), Sulfate (SO$_4^-$M$^+$), Sulfonate (SO$_3^-$M$^+$), carboxylate (COO$^-$M$^+$), a nonionic group, or a quaternary ammonium ion, wherein M+ is a counterion.

3. The surface active compound of claim 1 wherein $R_{13}$ is —[CH($R_{20}$)CH($R_{21}$)O]$_x$—, wherein x is an integer of from 0 to 100, and $R_{20}$ and $R_{21}$ are independently selected from any of the following:

H; —CH$_2$OH; phenyl; —CH$_2$Cl;

a $C_1$-$C_{30}$ straight or branched alkyl or alkenyl;

—CH$_2$OR$_{22}$ wherein $R_{22}$ is $C_1$-$C_{30}$ straight or branched alkyl or alkenyl, phenyl, or alkyl substituted phenyl; or R'COOCH$_2$— where R' is $C_1$-$C_{30}$ straight or branched alkyl or alkenyl.

4. A surface active compound according to structure D.XXX:

$$R_{18}-O-[(C_gH_{2g}O)_i-(C_hH_{2h}O)_j]_k-(CH_2)_b-R^{11}$$ (D.XXX)

wherein:
g is an integer from 2 to 4;
h is an integer from 2 to 4;
b is an integer from 0 to 1;
k is an integer from 0 to 100;
i is an integer from 0 to 40;
j is an integer from 0 to 40;
$R^{18}$ is an anionic group, a cationic group or a nonionic group;
$R^{11}$ is according to structure D.XII

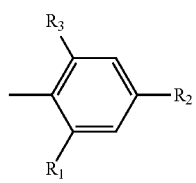
D.XII wherein $R_1$, $R_2$ and $R_3$ are independently selected from H, any of the following structures D.XIId, D.XIIIa, D.XIIIb, D.XIIIc, D.XIIId:

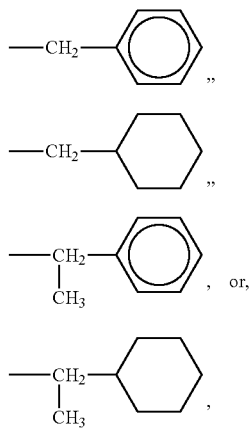

D.XIIIa

D.XIIIb

D.XIIIc

D.XIIId or a $C_4$-$C_{30}$ branched or linear alkyl group or alkenyl group;
wherein at least one of $R_1$, $R_2$ and $R_3$ is the $C_4$-$C_{30}$ branched or linear alkyl group or alkenyl group and at least one of $R_1$, $R_2$ and $R_3$ is selected from structure D.XIIIa, D.XIIIb, D.XIIIc, or D.XIIId.

5. The compound according to claim 4 wherein $R^{18}$ is —OH, —OCH$_3$, —OC$_2$H$_5$, —OC$_3$H$_7$, —OC$_4$H$_9$, —OC$_5$H$_{11}$, —OC$_6$H$_{13}$, —Cl, —Br, —CN, Phosphonate (—PO$_3^-$M$^+$), Phosphate (PO$_4^-$M$^+$), Sulfate (SO$_4^-$M$^+$), Sulfonate (SO$_3^-$M$^+$), carboxylate (COO$^-$M$^+$), a nonionic group, or a quaternary ammonium ion, wherein M+ is a cation including but not limited to H$^+$, Na$^+$, NH$_4^+$, K$^+$ or Li$^+$.

6. The compound according to claim 4 wherein:
g is an integer from 2 to 4;
h is an integer from 2 to 4;
b is an integer from 0 to 1;
k is an integer from 0 to 25;
i is an integer from 0 to 40;
j is an integer from 0 to 40;

$R^{11}$ is a tri-substituted aromatic group according to the structure D.XII

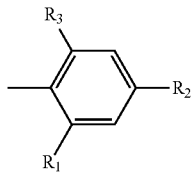
D.XII wherein $R_1$, $R_2$ and $R_3$ are independently selected from the following structures D.XIIIa, D.XIIIb, D.XIIIc, D.XIIId:

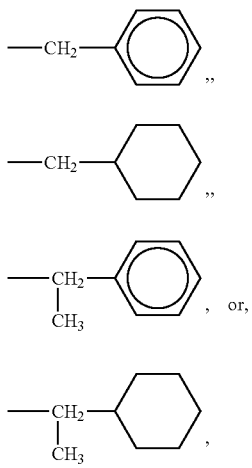

or a $C_6$-$C_{30}$ branched or linear alkyl group or alkenyl group; wherein at least one of $R_1$, $R_2$ and $R_3$ is the $C_6$-$C_{30}$ branched or linear alkyl group or alkenyl group and at least one of $R_1$, $R_2$ and $R_3$ is selected from structure D.XIIIa, D.XIIIb, D.XIIIc, or D.XIIId.

7. The compound of claim 1 wherein the $C_4$-$C_{30}$ branched or linear alkyl group or alkenyl group is a $C_6$-$C_{14}$ branched or linear alkyl group.

8. The compound of claim 4 wherein the $C_4$-$C_{30}$ branched or linear alkyl group or alkenyl group is a $C_6$-$C_{14}$ branched or linear alkenyl group.

9. The compound of claim 1 wherein the $C_4$-$C_{30}$ branched or linear alkyl group or alkenyl group is a $C_8$-$C_{12}$ branched or linear alkyl group.

10. The compound of claim 4 wherein the $C_4$-$C_{30}$ branched or linear alkyl group or alkenyl group is a $C_8$-$C_{12}$ branched or linear alkenyl group.

11. The compound of claim 1 wherein the $C_4$-$C_{30}$ branched or linear alkyl group or alkenyl group is a $C_4$-$C_{12}$ branched or linear alkyl group or alkenyl group.

12. The compound of claim 4 wherein the $C_4$-$C_{30}$ branched or linear alkyl group or alkenyl group is a $C_4$-$C_{12}$ branched or linear alkenyl group.

13. The compound of claim 6 wherein $R^{11}$ is a tri-substituted aromatic group according to the structure D.XII

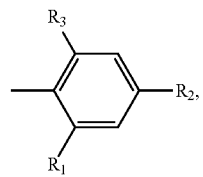
D.XII wherein $R_1$, $R_2$ and $R_3$ are independently selected from:
a styryl group, or
a $C_6$-$C_{30}$ branched or linear alkyl group or alkenyl group; wherein at least one of $R_1$, $R_2$ and $R_3$ is the $C_6$-$C_{30}$ branched or linear alkyl group or alkenyl group, and at least one of $R_1$, $R_2$ and $R_3$ is the styryl group.

14. The compound of claim 1 wherein $R^{11}$ is a tri-substituted aromatic group according to the structure D.XII-1

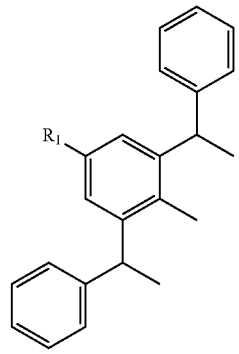
D.XII-1 wherein $R_1$, is the $C_4$-$C_{30}$ branched or linear alkyl group or alkenyl group.

15. The compound of claim 14 wherein the $C_4$-$C_{30}$ branched or linear alkyl group or alkenyl group is a $C_4$-$C_{12}$ branched or linear alkyl group or alkenyl group.

16. A low VOC latex coating composition comprising:
(a) at least one latex polymer;
(b) optionally, at least one pigment;
(c) water; and
(d) an additive present in an amount effective to impart freeze-thaw stability, having structure D.XII

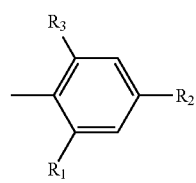
D.XII wherein $R_1$, $R_2$ and $R_3$ are independently selected from H, any of following structures D.XIIIa, D.XIIIb, D.XIIIc, D.XIIId:

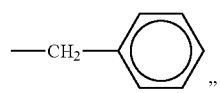
D.XIIIa

-continued

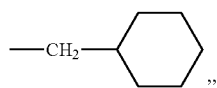 D.XIIIb

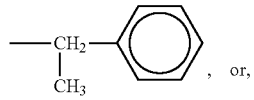 , or, D.XIIIc

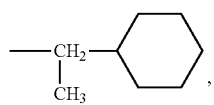 , D.XIIId or a $C_4$-$C_{30}$ branched or linear alkyl group or alkenyl group;

wherein at least one of $R_1$, $R_2$ and $R_3$ is the $C_4$-$C_{30}$ branched or linear alkyl group or alkenyl group, and at least one of $R_1$, $R_2$ and $R_3$ is selected from structure D.XIIIa, D.XIIIb, D.XIIIc, or D.XIIId.

17. A method for imparting freeze-thaw stability on a low VOC coating composition comprising adding to the composition an effective amount of an additive according to structural formula D.XII

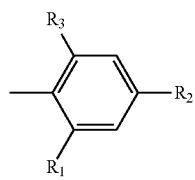 D.XII wherein $R_1$, $R_2$ and $R_3$ are independently selected from H, any of following structures D.XIIIa, D.XIIIb, D.XIIIc, D.XIIId:

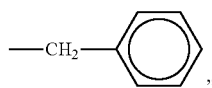 D.XIIIa

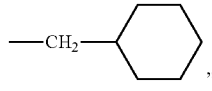 D.XIIIb

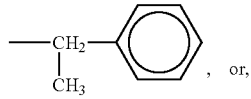 , or, D.XIIIc

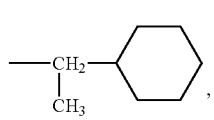 , D.XIIId or a $C_4$-$C_{30}$ branched or linear alkyl group or alkenyl group;

wherein at least one of $R_1$, $R_2$ and $R_3$ is the $C_4$-$C_{30}$ branched or linear alkyl group or alkenyl group, and at least one of $R_1$, $R_2$ and $R_3$ is selected from structure D.XIIIa, D.XIIIb, D.XIIIc, or D.XIIId wherein the coating composition comprises a latex polymer.

18. The method of claim 17 wherein the effective amount is an amount of the additive greater than about 0.5% by weight of the polymer.

19. The method of claim 17 wherein the effective amount is an amount of the additive greater than about 1.3% by weight of the polymer.

20. The method of claim 17 wherein the effective amount is an amount of the additive greater than about 1.6% by weight of the polymer.

21. The method of claim 17 wherein the effective amount is an amount of the additive greater than about 1% by weight of the polymer.

* * * * *